(12) United States Patent
Evans

(10) Patent No.: US 6,347,329 B1
(45) Date of Patent: *Feb. 12, 2002

(54) ELECTRONIC MEDICAL RECORDS SYSTEM

(75) Inventor: Jae A. Evans, Carlsbad, CA (US)

(73) Assignee: Macneal Memorial Hospital Assoc., Berwyn, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/628,390

(22) Filed: Aug. 1, 2000

Related U.S. Application Data

(63) Continuation of application No. 09/333,170, filed on Jun. 14, 1999, which is a continuation of application No. 08/721,182, filed on Sep. 27, 1996.

(51) Int. Cl.[7] .............................................. G06F 15/16
(52) U.S. Cl. ....................... 709/202; 709/205; 345/326; 705/2; 705/3
(58) Field of Search ................................ 709/202, 205, 709/217; 345/326; 705/2, 3

(56) References Cited

U.S. PATENT DOCUMENTS

| | | |
|---|---|---|
| 3,872,448 A | 3/1975 | Baker |
| 4,315,309 A | 2/1982 | Coli |
| 5,065,315 A | 11/1991 | Garcia |
| 5,099,424 A | 3/1992 | Schneiderman |
| 5,277,188 A | 1/1994 | Selker |
| 5,416,695 A | 5/1995 | Stutman et al. |
| 5,659,741 A | 8/1997 | Eberhardt |

OTHER PUBLICATIONS

Declaration of Hollon H. Bridges, Jr., dated Sep. 24, 1996.
Declaration of Jae A. Evans, dated Sep. 27, 1996.
Declaration of Marion Neal, dated Sep. 26, 1996.
Declaration of David Printz, dated Sep. 26, 1996.
Kleinholz, et al. "Supporting Cooperative Medicine: The Bermed Project," IEEE MultiMedia, vol. 1, No. 4, Dec. 21, 1994, pp. 44–53.

*Primary Examiner*—Thomas R. Peeso
(74) *Attorney, Agent, or Firm*—Knobbe, Martens, Olson & Bear, LLP.

(57) ABSTRACT

A medical records system that creates and maintains all patient data electronically. The system captures patient data, such as patient complaints, lab orders, medications, diagnoses, and procedures, at its source at the time of entry using a graphical user interface having touch screens. Using pen-based portable computers with wireless connections to a computer network, authorized healthcare providers can access, analyze, update and electronically annotate patient data even while other providers are using the same patient record. The system likewise permits instant, sophisticated analysis of patient data to identify relationships among the data considered. Moreover, the system includes the capability to access reference databases for consultation regarding allergies, medication interactions and practice guidelines. The system also includes the capability to incorporate legacy data, such as paper files and mainframe data, for a patient.

1 Claim, 26 Drawing Sheets

Azron Ink Writer—Denson, Bob W.

File  Edit  Zoom  Options

DAMON CLINICAL LABORATORY
3231 South Euclid Ave.
Barwyn, Illinois 60402
Leonas G. Bakaris, M.D.

BRIDGEVIEW INT. MED. CTR.    71
7217 W. 84TH STREET          SA
BRIDGEVIEW, IL. 60455

| | | | 54076,22005 | | | |
|---|---|---|---|---|---|---|
| | | PATIENT NAME | | | | |
| | | DRNSON, BOB | | | | |
| | | ACCESSION NO. | AGE | SEX | TV/SOURCE | |
| | | 3156443 | 39 | M | | |
| | | REFERRING PHYSICIAN | | | CLIENT NO. | |
| | | KARIDES | | | 84699 | |
| | | ORDER STATUS | COLLECTION DATE: TIME | | | |
| | | COMPLETE | 01/17/89 | | 03:30 PM | |
| TEST | OUTSIDE RANGE | WITHIN RANGE | UNITS | REFERENCE | | |
| CHEM 24 | | | | | | |
| GLUCOSE | — | 88 | MG/DL | 70–11 | | |
| CREATININE | — | 0.9 | MG/DL | 0.6–1. | | |
| BUN | — | 13 | MG/DL | 6–21 | | |
| BUN/CREATININE RATIO | — | 14.4 | | 7.4–23 | | |
| SODIUM | — | 147 | MEQ/L | 134–14 | | |
| POTASSIUM | — | 5.2 | MEQ/L | 3.5–5. | | |
| CHLORIDE | — | 110 | MEQ/L | 95–11 | | |
| CO2-AS BICARBONATE | 23.1 | | MEQ/L | 24–32 | | |
| URIC ACID | — | 4.2 | MG/DL | 2.5–6. | | |
| BILIRUBIN, TOTAL | — | 0.3 | MG/DL | 0.2–1. | | |
| BILIRUBIN, DIRECT | — | Out of Range 49 | MG/DL | 0.0–0. | | |
| BILIRUBIN, INDIRECT | — | | MG/DL | 0.1–1. | | |
| TRIGLYCERIDE | — | 197 | MG/DL | 10–25 | | |
| CHOLESTEROL | — | 10.1 | MG/DL | 120–20 | | |
| LEIM | — | 4.0 | MG/DL | 8.5–10 | | |
| PHOSPHORUS | — | 109 | MMG/DL | 2.4–4. | | |
| ALK PHOSPHAYASE, COLOR | 258 H | | U/L | 25–11 | | |
| LDH | — | 21 | U/L | 85–21 | | |
| SGDT | — | 23 | U/L | 0–40 | | |
| SGPT | — | 6.8 | | 0–50 | | |
| PBDTEIN, TOTAL | — | | GM/DL | 6.0–8. | | |

Dr. Phil Daley – Internal Medicine

Selected Patient: Denson, Bob W.

Tabs: Practice Guidelines | List All | Patient Data
Medication Date | History | Problem List | Encounter Data
Progress Notes | Laboratory | Clinical Data

Laboratory

| Date | Description | Reviewed |
|---|---|---|
| 4/9/94 | CBC | |
| 4/8/94 | Slide | X |
| 1/29/91 | SED Rate, SMAC, CBC, Wintrobe-Allied | X |
| 1/17/89 | Chem24, Urinalysis | X |
| 6/9/88 | Cholesterol | X |

New Forms:

Patient Encounter for Denson, Bob W.

Complete Diagnosis List by Section: Respiratory System

Complete Procedure List by Section: Medicine

Diagnoses
Sort By: ○ Code  ● Description

| Code | Description |
|---|---|
| 477.0 | ALLERGIC RHINITIS DUE TO POLLEN |
| 477.9 | ALLERGIC RHINITIS, CAUSE |
| 501 | ASBESTOSIS |
| ▲ 493 | ASTHMA |
| 493.9 | ASTHMA, UNSPECIFIED |
| 493.91 | ASTHMA,UNSPECIFIED TYPE, WITH |
| 493.90 | ASTHMA, UNSPECIFIED TYPE, |
| 482.9 | BACTERIAL PNEUMONIA, |
| 495.1 | BAGASSOSIS |
| 5.1 | BOTULISM |
| 494 | BRONCHIECTASIS |
| 506.0 | BRONCHITIS AND PNEUMONITIS DUE |
| 490 | BRONCHITIS, NOT SPECIFIED AS |

Procedures
Sort By: ○ Code  ● Description

| Code | Description |
|---|---|
| 95823 | ACTIVATION EEG |
| 97531 | ADDED KINETIC THERAPY |
| ▲ 94642 | AEROSOL INHALATION TREAMENT |
| 94665 | AEROSOL OR VAPOR INHALATIONS |
| 94664 | AEROSOL OR VAPOR INHALATIONS |
| 94640 | AIRWAY INHALATION TREATMENT |
| 95199 | ALLERGY IMMUNOLOGY SERVICES |
| 95044 | ALLERGY PATCH TESTS |
| 95028 | ALLERGY SKIN TESTS |
| 95004 | ALLERGY SKIN TESTS |
| 95024 | ALLERGY SKIN TESTS |
| 93788 | AMBULATORY BP ANALYSIS |
| 93784 | AMBULATORY BP MONITORING |

Selected Diagnoses
| 493 | ASTHMA |

[Add] [Remove] [Clear]

Add Note

[OK]   [Cancel]

Selected Procedures
| 94642 | AEROSOL INHALATION TREA |

[Add] [Remove] [Clear]

*FIG. 20*

ELECTRONIC MEDICAL RECORDS SYSTEM

RELATED APPLICATIONS

This application is a continuation of U.S. application No. 09/333,170 filed on Jun. 14, 1999 which in turn is a cont. of U.S. application No. 08/721,182 filed on Sep. 27, 1996.

BACKGROUND OF THE INVENTION

1. Field of the Invention

The present invention relates to electronic healthcare systems, and more particularly, to a system for storage and retrieval of electronic medical records in a computer environment, such as a local or wide area network including portable computers.

2. Description of Related Technology

Healthcare providers, such as physicians, create large volumes of patient information during the course of their business at healthcare facilities, such as hospitals, clinics, laboratories and medical offices. For example, when a patient visits a physician for the first time, the physician generally creates a patient file including the patient's medical history, current treatments, medications, insurance and other pertinent information. This file generally includes the results of patient visits, including laboratory test results, the physician's diagnosis, medications prescribed and treatments administered. During the course of the patient relationship, the physician supplements the file to update the patient's medical history. When the physician refers a patient for treatment, tests or consultation, the referred physician, hospital, clinic or laboratory typically creates and updates similar files for the patient. These files may also include the patient's billing, payment and scheduling records.

Healthcare providers can use electronic data processing to automate the creation, use and maintenance of their patient records. For example, in U.S. Pat. No. 5,277,188, assigned to New England Medical Center Hospitals, Inc., Selker discloses a clinical information reporting system having an electronic database including electrocardiograph related patient data. Similarly, Schneiderman discloses a computer system for recording electrocardiograph and/or chest x-ray test results for a database of patients in U.S. Pat. No. 5,099,424. In U.S. Pat. No. 4,315,309, Coli discloses a patient report generating system for receiving, storing and reporting medical test data for a patient population. Mitchell, in U.S. Pat. No. 3,872,448, likewise discloses a system for automatically handling and processing hospital data, such as patient information and pathological test information using a central processing apparatus. In U.S. Pat. No. 5,065,315, Garcia discloses a computerized scheduling and reporting system for managing information pertinent to a patient's stay in the hospital. However, these electronic data processing systems can not handle patient data in the wide variety of data formats typically produced by healthcare providers, such as physicians, laboratories, clinics and hospitals.

Physicians often use paper based forms and charts to document their observations and diagnosis. Laboratories also produce patient data in numerous forms, from x-ray and magnetic resonance images to blood test concentrations and electrocardiograph data. Clinics and hospitals may use a combination of paper based charts and electronic data for patient records. The same patient data may exist in remote patient files located at clinics, hospitals, laboratories and physicians' offices. Similarly, patient files at one healthcare provider typically have different information than patient files at another healthcare provider. When in use, patient files are generally not available to other healthcare providers. In addition, at the time of creation, patient data is generally not available for use by remotely located healthcare providers. Moreover, relationships among specific patient data, such as abnormal laboratory test results, prescribed medications to address the abnormality, and specific treatments administered by the physician, may not be apparent within a patient file.

In the current environment, specific patient data is difficult to access when needed for analysis. The creation of patient data in remote locations exacerbates this problem. In addition, the wide variety of data formats for patient data hinders electronic processing and maintenance of patient files. Moreover, the use of a patient's file by one healthcare provider can preclude its simultaneous use by another healthcare provider. Ongoing consolidation of healthcare providers into large health maintenance organizations (HMOs) and preferred provider organizations (PPOs) create issues in the transfer and maintenance of patient data in large enterprises having numerous remote locations. Under these circumstances, healthcare providers have difficulty providing effective treatment for their patients.

SUMMARY OF THE INVENTION

The electronic medical record (EMR) system of the present invention automates and simplifies existing methods of patient chart creation, maintenance and retrieval. In contrast to other systems, the present invention creates and maintains all patient data electronically and thus can eliminate or supplement creating and maintaining of physical data records. The EMR system furnishes healthcare providers with an intuitive, easy-to-use, icon-based interface that enables them to capture and analyze patient data quickly and efficiently. Using the present invention, healthcare providers enter patient data immediately at the point of care. Thus, the EMR system captures each piece of data at its source at the time of entry to provide a complete audit trail for all patient data. In this manner, the EMR system transforms a patient chart from a static record of a few clinical interactions into a dynamic, real-time comprehensive record linked to an enterprise-wide clinical database. In addition, the EMR system of the present invention includes the capability to manage a wide variety of patient data formats, including patient data from external sources, such as laboratories and pharmacies. The EMR system can also incorporate a patient's legacy data, such as a paper chart, into the patient record as well as legacy data from mainframe computers.

The present invention likewise provides instant access to a patient's electronic medical record by authorized healthcare providers from any geographical location. Thus, the EMR system enables authorized healthcare providers to access and update patient files using wireless pen-based personal computers. To enable complete replacement of physical records, the present invention permits healthcare providers, such as physicians or nurse practitioners, to electronically annotate patient data. Thus, a healthcare provider can acknowledge reviewing patient data, provide instructions, such as prescriptions for medication to administer to a patient, and approve recommendations for treatment by other providers, all by electronically annotating a patient's record. In addition, authorized healthcare providers can access a record while other providers use the same record allowing for real-time collaboration. The availability of electronic data permits instant, sophisticated analysis of patient data. Moreover, the EMR system enables enhanced analysis of patient data by providing access to reference databases for diagnosis, procedures and medication.

One aspect of the present invention includes a medical records system, comprising a point of care system to capture patient data at a point of care and a patient data repository, in communication with the point of care system and with external systems, to store and organize the patient data for access by the point of care system.

Another aspect of the present invention includes a medical records system comprising a point of care system to capture data in a patient record at a point of care, wherein the patient record includes a patient identifier and at least one data structure including the patient identifier and the data.

Yet another aspect of the present invention includes a medical records system comprising a point of care system to capture data at a point of care and a patient data repository, in communication with the point of care system and with external systems to store and organize the data in a patient record for access by the point of care system, wherein the patient record includes a patient identifier and at least one data structure including the patient identifier and the data.

In addition, another aspect of the present invention includes a method of using an electronic medical records system, comprising the steps of capturing patient data electronically at the point of care, organizing the patient data so as to form a patient record, filing the patient record, and retrieving the patient record to access the patient data for use in the care of a patient.

Yet another aspect of the present invention includes a method of retrieving patient data in an electronic medical records system having a patient data repository, comprising the steps of obtaining a patient identifier, locating a patient record corresponding to the patient identifier in the patient data repository, and determining the location of the patient data within the patient record.

Another aspect of the present invention includes a method of managing a patient data repository having a cache and a data archive, comprising the steps of monitoring a status of data within the cache, and moving the data to the data archive when the status exceeds a threshold.

Still another aspect of the present invention includes a method of communicating with an external source having an interface to an electronic medical records system, comprising the steps of finding an interface for the external source, connecting to the external source using the interface, and converting patient data for transfer between the external source and the electronic medical records system.

BRIEF DESCRIPTION OF THE DRAWINGS

FIG. 7 shows an example of an annotate window of the point of care system of FIG. 4.

FIG. 19 shows an example of a graphical user interface of the point of care system of FIG. 4 having a reference access button and a medication manager button.

FIG. 20 shows an example of a graphical user interface for the diagnosis module and the procedure module of the reference database of FIG. 18.

DETAILED DESCRIPTION OF THE PREFERRED EMBODIMENTS

The following detailed description of the preferred embodiments presents a description of certain specific embodiments to assist in understanding the claims. However, one may practice the present invention in a multitude of different embodiments as defined and covered by the claims.

For convenience, the description comprises three sections: EMR System Architecture and Overview, EMR System Configurations and Summary. The first section provides an overview of the EMR system architecture, the following section describes EMR system applications and preferred embodiments for practicing the EMR system of the present invention, and the remaining section summarizes advantageous features of the present invention.

I. EMR System Architecture and Overview

Figure 1:
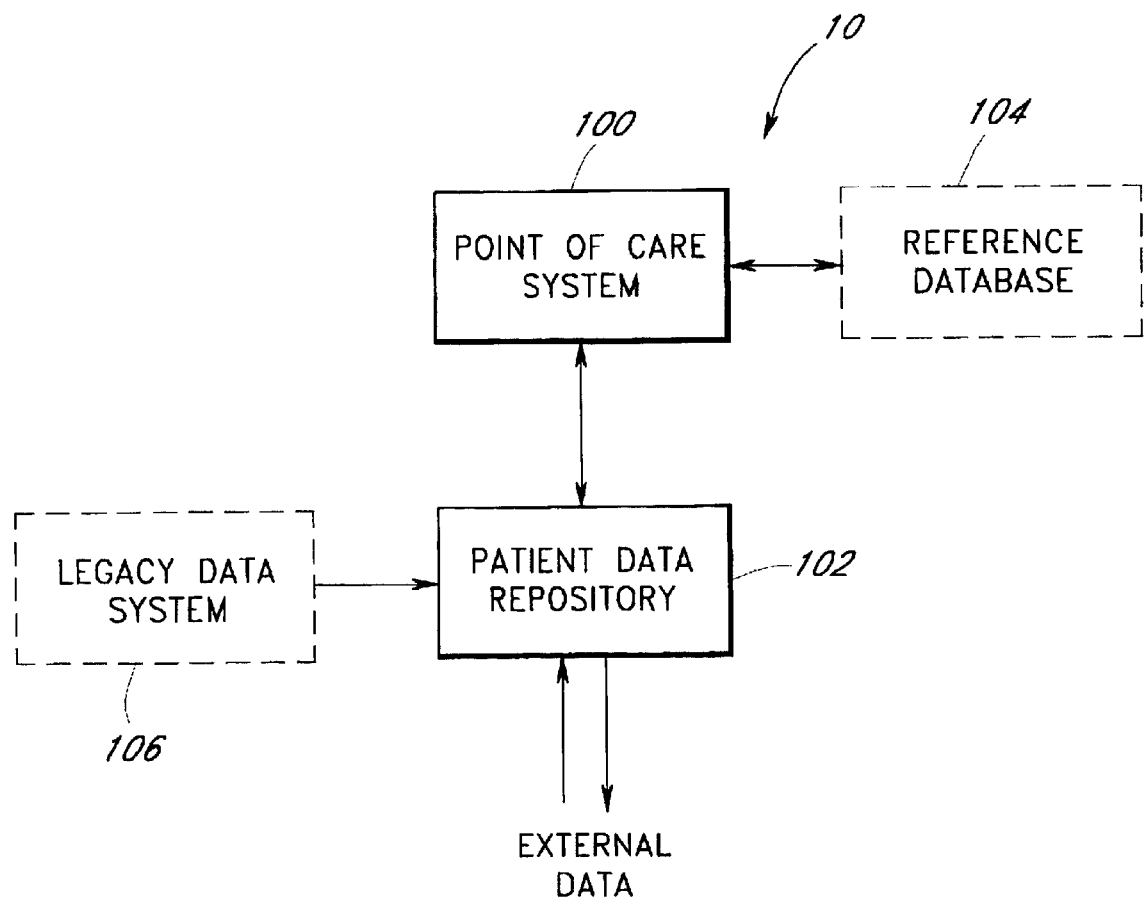
FIG. 1 is a block diagram illustrating the electronic medical record (EMR) system architecture of the present invention.

FIG. 1 illustrates the architecture of the EMR system. Healthcare providers, such as physicians, at hospitals, laboratories and clinics, generally capture and access patient data using a point of care system 100 that communicates with a patient data repository 102. Patient data, such as vital signs, x-ray images and laboratory results, resides in the patient data repository 102. The patient data repository 102 also communicates with external sources to obtain patient data, such as laboratory test results and x-ray images, and to transfer patient information, such as prescriptions for medication, from the EMR system to other healthcare providers. The point of care system 100 captures patient data in realtime at the point of care, that is, where healthcare providers interact with their patients. For example, physicians can use a point of care system 100 to enter, access, process, analyze and annotate data from patient records in real-time at the point of care. Thus, using the point of care system 100, a physician, who has many patients in a hospital, can visit each patient in their room, access their electronic patient record there, enter results of the current examination, evaluate their medical history, electronically annotate their x-rays images and prescribe medications and treatments instantaneously as the point of care system 100 captures and organizes patient data into the patient record stored in the patient data repository 102. The point of care system 100 may likewise communicate with a reference database 104 to assist a healthcare provider in making diagnoses, prescribing medications and administering treatments. Moreover, the patient data repository 102 may also communicate with a legacy data system 106 to access pertinent patient data in paper files and mainframe electronic databases.

Figure 2:
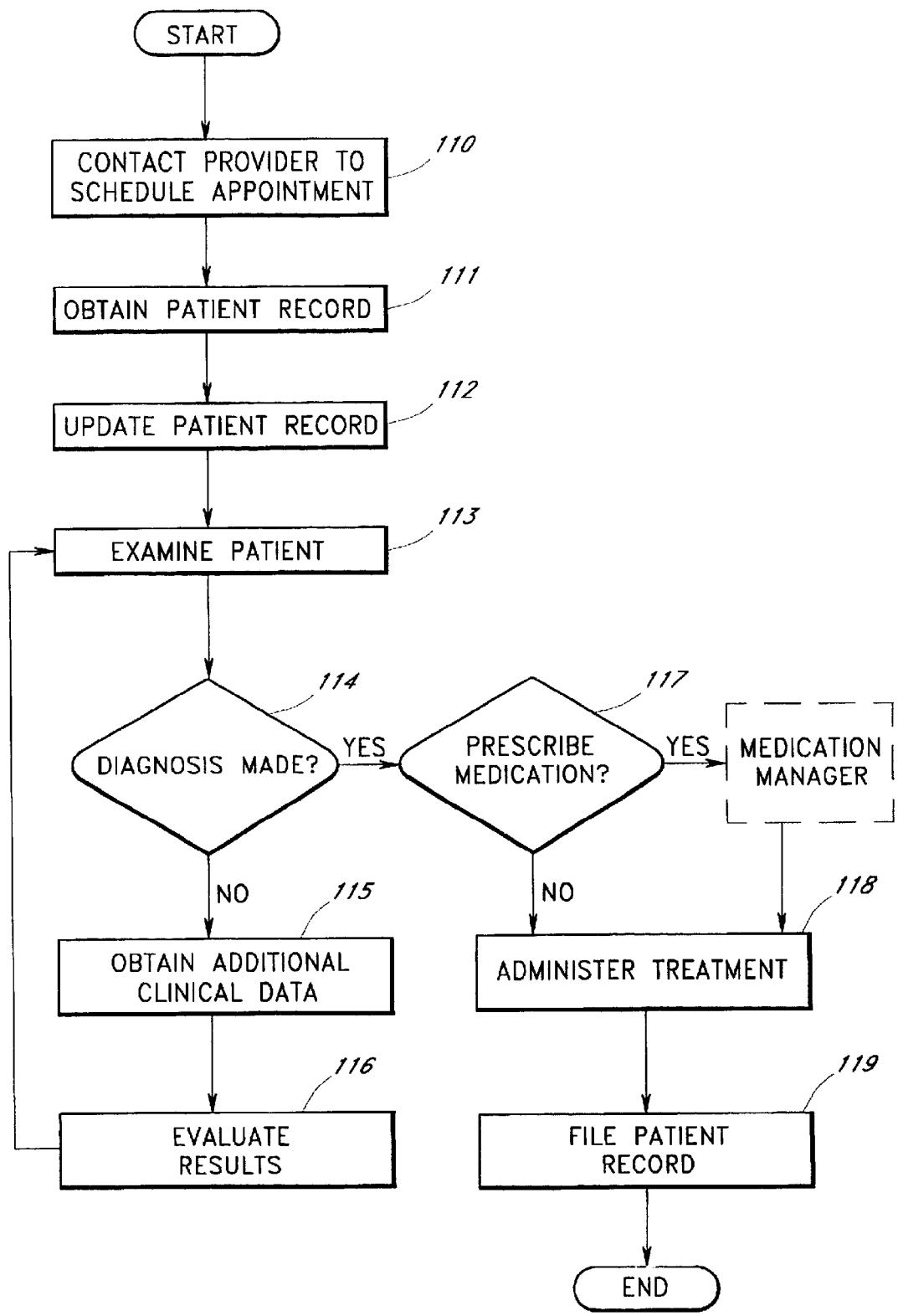
FIG. 2 is a flowchart illustrating the process flow of the EMR system of the present invention.

Referring now to FIG. 2, a flowchart illustrates the operation of the EMR system. For example, a patient having a complaint contacts a healthcare provider 110, such as a physician, to schedule an appointment. The EMR system obtains the patient record 111 from the patient data repository 102 (FIG. 1) prior to the scheduled appointment. The EMR system is also capable of handling patients on a walk-in basis by scheduling an appointment and requesting the patient's record immediately thereafter. The EMR system updates the patient record 112 to include the complaint and other information pertinent to the appointment, such as insurance information. A healthcare provider, such as a physician, examines the patient 113 using the point of care system 100 (FIG. 1) to make a diagnosis and to treat the patient's condition. As determined at 114, if a diagnosis is not possible on the basis of this examination, the physician may need to obtain additional clinical data 115, such as laboratory tests and x-rays. When available, the physician uses the point of care system 100 (FIG. 1) to evaluate the results 116 and to examine the patient 113 again in light of the results. Upon making a diagnosis, the physician may need to prescribe medications 117 for the patient's condition. Similarly, the physician may need to administer a treatment 118 to address the patient's condition. At the conclusion of the patient's visit, the EMR system files the patient's record 119 in the patient data repository 102 (FIG. 1) for future reference.

Figure 3:
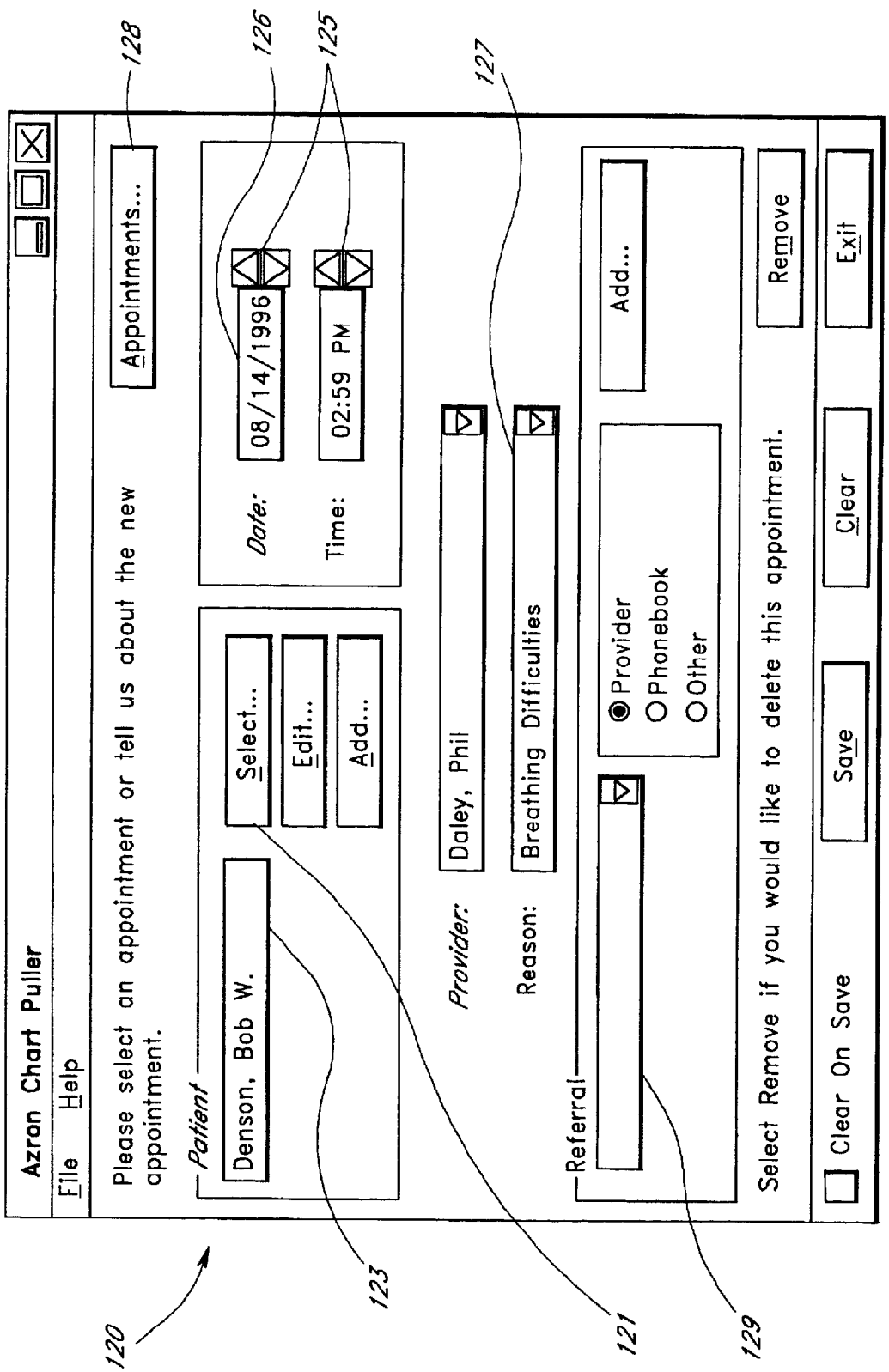
FIG. 3 shows an example of a graphical user interface of the EMR system useful for the scheduling of a patient appointment as shown in FIG. 2.

In a preferred embodiment, the EMR system includes graphical user interfaces to access system functions. For example, as shown in FIG. 3, a chart puller window 120 enables a healthcare provider to schedule a patient appointment using its point and click interface. To schedule an appointment, a healthcare provider activates the select button 121 with a pointing device, such as a mouse or electronic pen, to obtain a list of patients. The healthcare provider then scans the list to select the name of the appropriate patient using a pointing device. The EMR system places the name of the selected patient in the patient box 123. Similarly, the healthcare provider uses the up/down buttons 125 to select an appointment date and an appointment time. An adjacent box, such as the date box 126, displays the selected date and time. Lastly, the healthcare provider enters a textual description of the patient's complaint in a reason box 127. Note that the healthcare provider can review prior or future scheduled appointments by clicking on the appointments button 128. Similarly, the healthcare provider can track referrals by entering the identity of persons who referred this patient to their care in the referral box 129.

Figure 4:
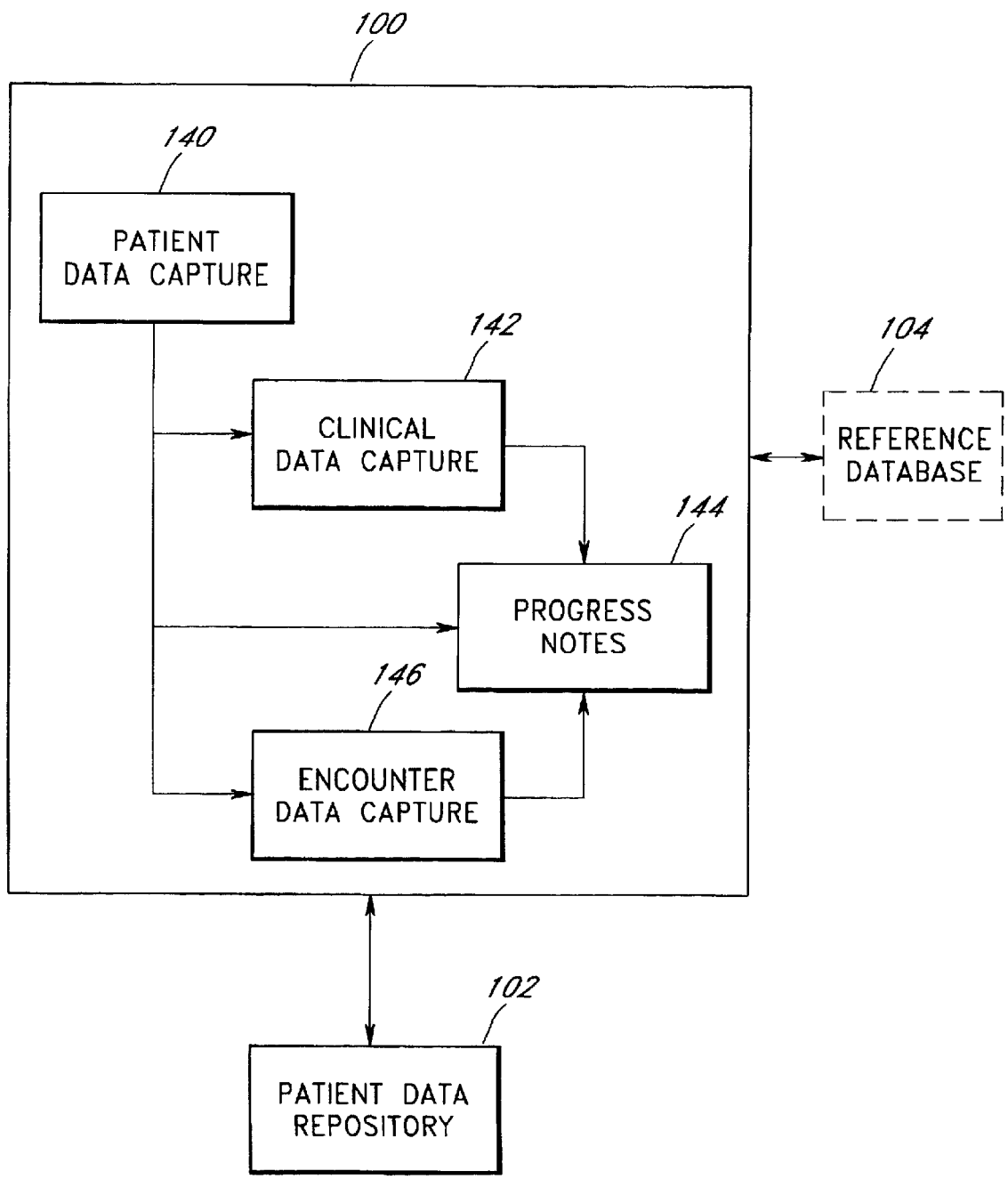
FIG. 4 is a block diagram illustrating the structure of the point of care system of FIG. 1.

Referring now to FIG. 4, a block diagram illustrates the structure of the point of care system 100. The point of care system 100 includes the following modules: a patient data capture 140, a clinical data capture 142, progress notes 144 and an encounter data capture 146. During a patient visit, the healthcare provider (not shown) can enter, review and annotate patient information, such as family history, appointments, current medications and complaints, using the patient data capture 140. The healthcare provider can likewise enter, review and annotate clinical data obtained during the visit, such as body temperature and blood pressure, using the clinical data capture 142. Similarly, the healthcare provider can enter laboratory data for patients with the clinical data capture 142. The clinical data capture 142 communicates with the patient data capture 140 to assist in identifying needs for further clinical data. For example, a family history of high blood pressure may indicate a need to obtain the patient's blood pressure during the visit. The patient data capture 140 also communicates with the encounter data capture 146, where a healthcare provider can enter, review and annotate data regarding diagnoses and procedures administered to the patient. Moreover, the healthcare provider can use the progress notes 144 to summarize details of the patient's condition and to review the patient's progress over time. Thus, the progress notes 144 communicates with the patient data capture 140, the clinical data capture 142 and the encounter data capture 146.

Figure 5:
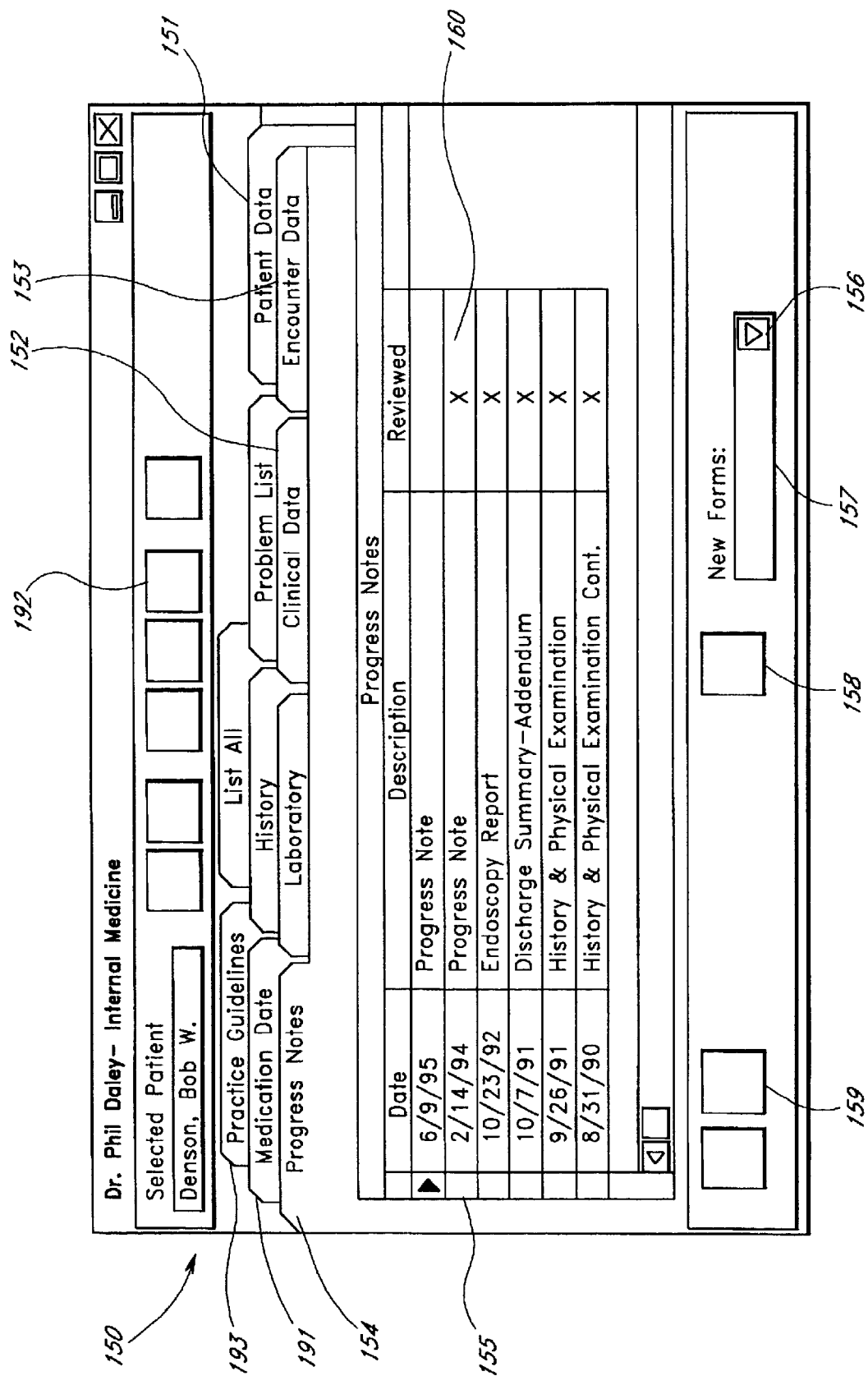
FIG. 5 shows an example of a graphical user interface of the point of care system of FIG. 4.

Referring now to FIG. 5, in a preferred embodiment, the point of care system 100 (FIG. 1) includes a graphical user interface having a patient chart window 150 to capture patient information. The point of care system 100 presents a patient record graphically using a tabbed layout to organize patient data. The patient chart window 150 includes tabs for patient data 151, clinical data 152, encounter data 153 and progress notes 154. Pointing and clicking on a tab on the patient chart window 150 opens a folder window 155 where a healthcare provider can enter and review patient data within the folder. For example, to activate progress notes 144 (FIG. 4), the healthcare provider selects the progress notes tab 154 to display a list of progress note data in the folder window 155. In a similar manner, to activate the patient data capture 140, the clinical data capture 142 or the encounter data capture 146, one selects the patient data tab 151, the clinical data tab 142, or the encounter data tab 153, respectively.

Figure 6:
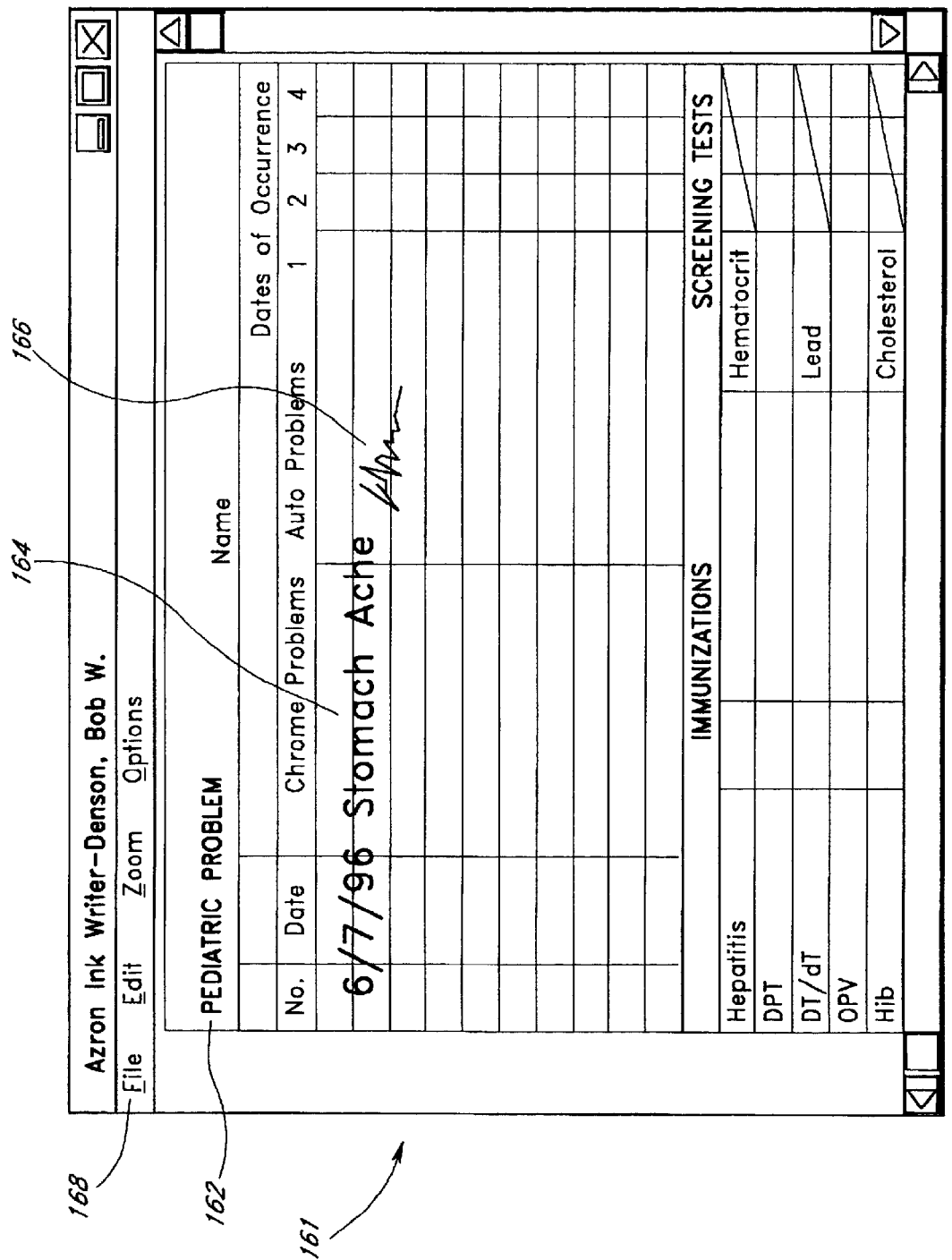
FIG. 6 shows an example of a new form window of the point of care system of FIG. 4.

To enter patient data, the healthcare provider clicks on the scroll down button 156 to select a form from a list of available forms to enter patient data. This activates the new forms box 157. The provider then points and clicks on the new form button 158. For example, FIG. 6 shows a new form window 161 displaying the pediatric problem form 162 selected by the healthcare provider using the scroll down button 156 (FIG. 5). The healthcare provider fills out the pediatric problem form 162 using an input device, such as a keyboard, a mouse or an electronic pen. For example, the provider uses a keyboard to enter text "Jun. 7, 1996 Stomach Ache" 164 and an electronic pen to enter initials 166 for identification. When done with patient data entry, the provider exits the form using the File Menu 168 and the point of care system 100 returns the provider to the patient chart window 150 (FIG. 5). Referring back to FIG. 5, the new form appears as the top entry of the list in the folder window 155.

Figure 8:
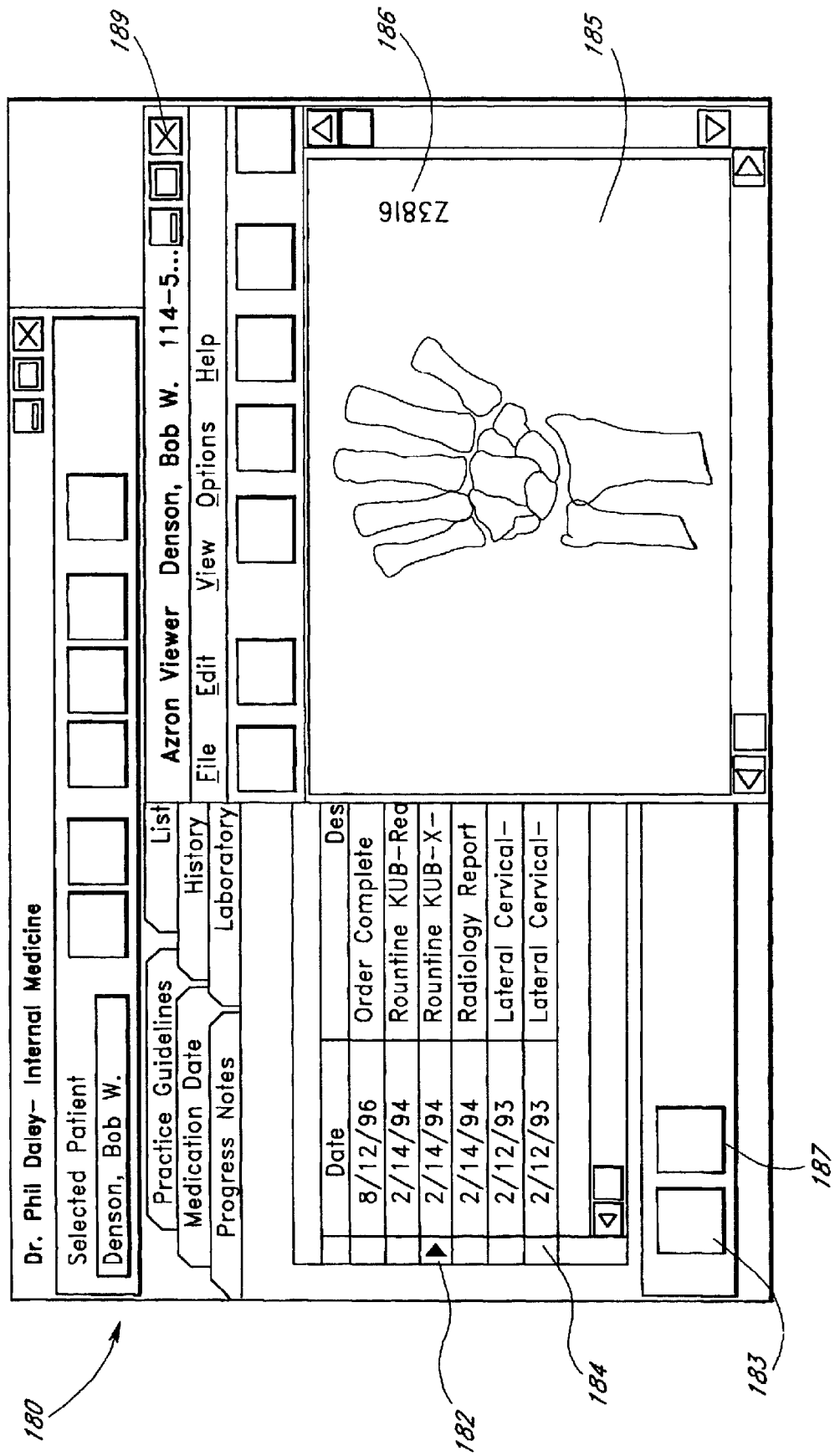
FIG. 8 shows an example of a viewer window displaying an image of patient data of the point of care system of FIG. 4.

Similarly, to annotate patient data, the healthcare provider first selects an item to annotate by pointing and clicking on the item in a list displayed in the folder window 155. The provider then clicks on the annotate button 159 to open the item in an annotate window 170, as shown in FIG. 7. For example, the annotate window 170 of FIG. 7 displays a blood test result 172. As before, the healthcare provider annotates the blood test result document 172 using an input device, such as a keyboard, a mouse or an electronic pen. For example, the provider uses a keyboard to enter text "Out of Range" 174 and an electronic pen to circle 176 the out of range result. When done with annotations, the provider exits the form using the File Menu 178 and the point of care system 100 returns the provider to the patient chart window 150 (FIG. 5). Note that the point of care system 100 tracks the review of patient data and identifies reviewed files with a mark 160 in the folder window 155. By annotating patient data, a healthcare provider, such as a physician, can acknowledge reviewing patient data, provide instructions, such as directions for additional tests and procedures or prescriptions for medication to administer to the patient, and approve recommendations for treatment by other healthcare providers. Lastly, as shown in FIG. 8, a healthcare provider uses the patient chart window 180 to view patient data. First, the healthcare provider selects a view item 182 by either pointing and clicking twice on the item in a list displayed in the folder window 184 or by pointing at the item in the list and pressing the view button 183. The double click opens a viewer window 185 to display the view item 182. For example, the viewer window 185 of FIG. 8 displays an x-ray 186. As before, the healthcare provider may annotate the x-ray 186 with comments and observations by clicking on the annotate button 187. The healthcare provider may likewise close the viewer window 185 by clicking on the close button 189.

Figure 9:
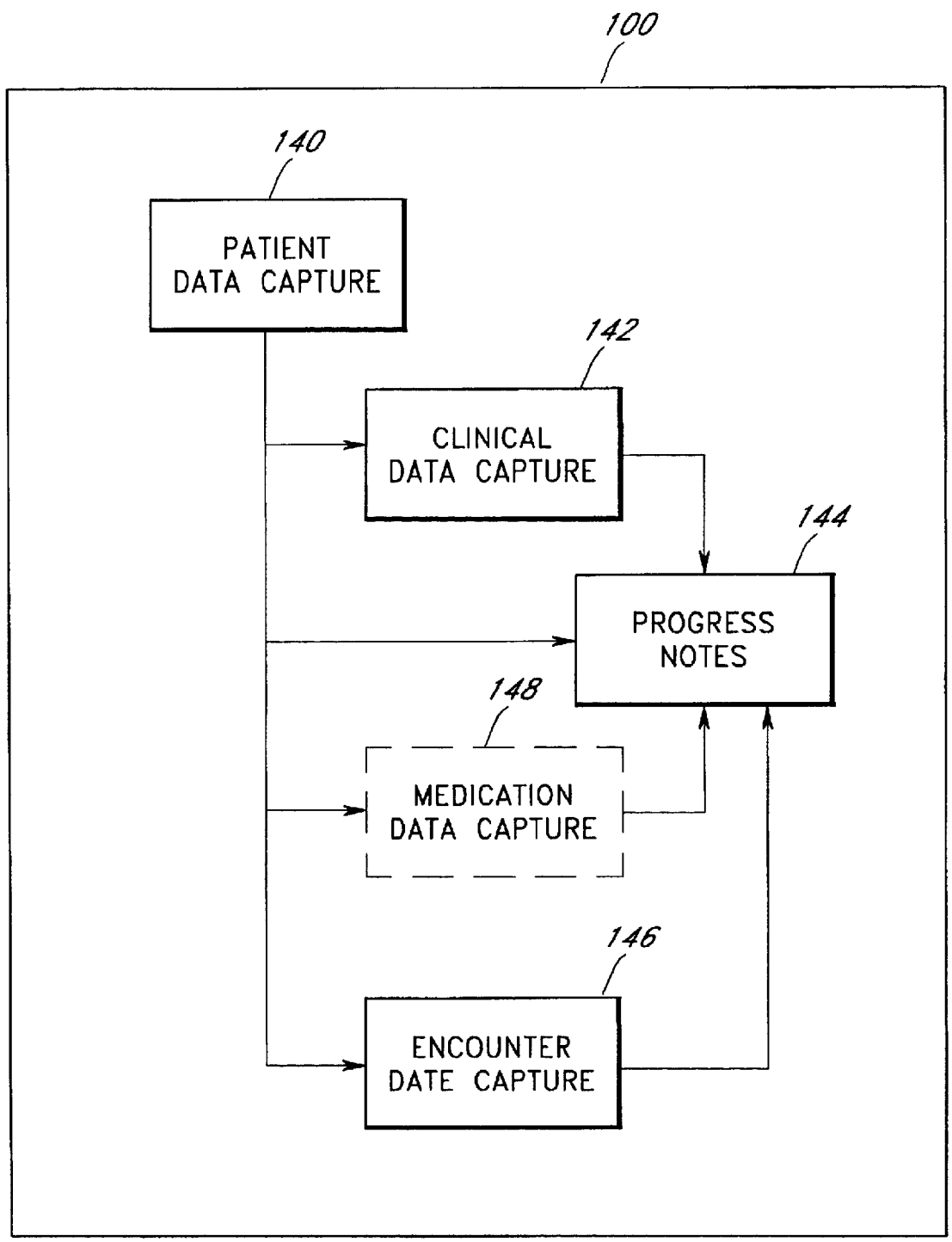
FIG. 9 is a block diagram illustrating the structure of a medication data capture in the point of care system of FIG. 4.
Figure 10:
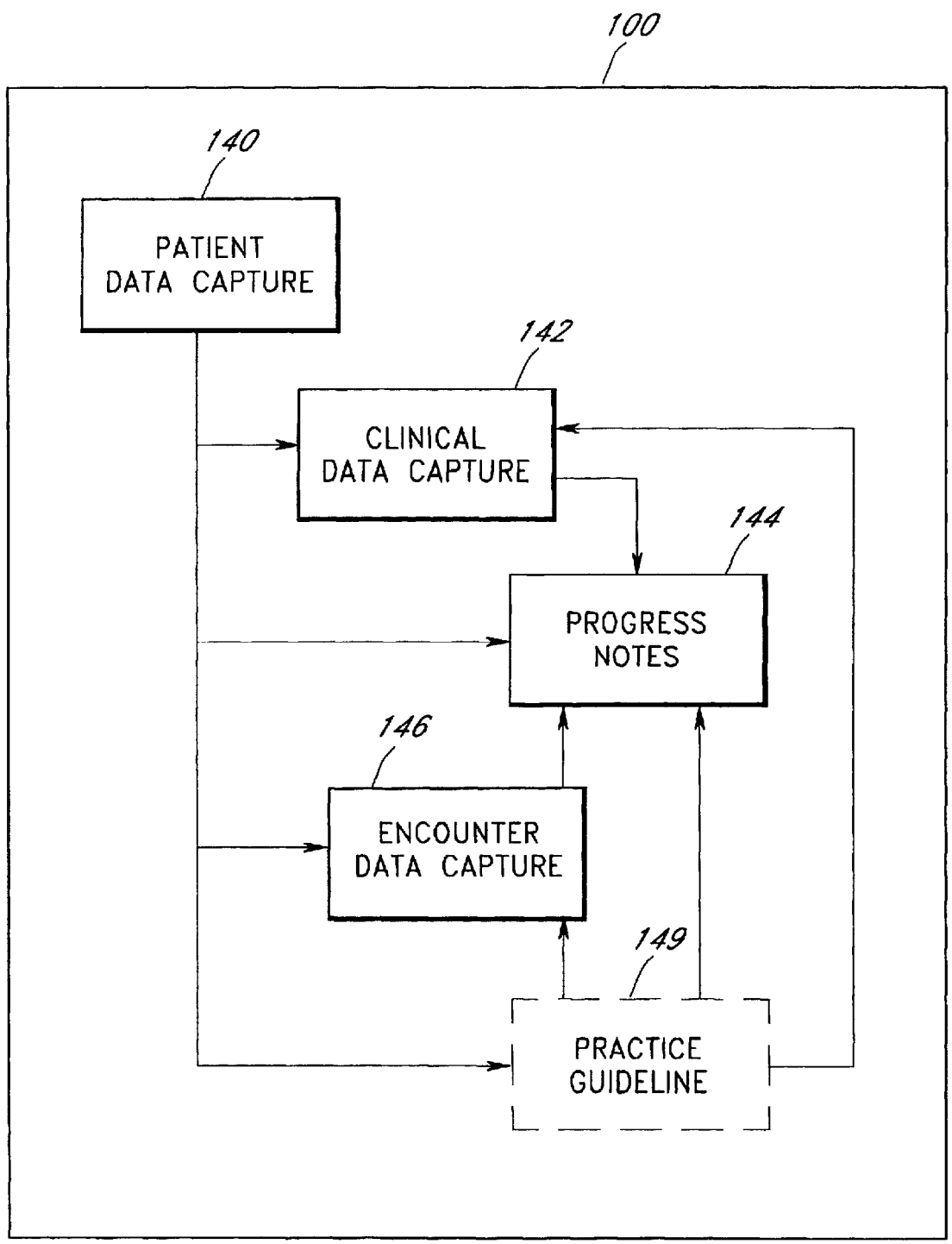
FIG. 10 is a block diagram illustrating the structure of a practice guideline in the point of care system of FIG. 4.

Certain additional structures in the point of care system 100 (FIG. 1) will now be discussed with reference to FIGS. 9, 10 and 11. Referring now to FIG. 9, an optional medication data capture 148 supplements the structure of the point of care system 100 of FIG. 4. A medication data capture 148 allows a healthcare provider to monitor a patient's medications. The medication data capture 148 communicates with the patient data capture 140 to account for medications the patient is currently taking. The medication data capture 148 similarly communicates with the progress notes 144, where a practitioner can monitor changes in a patient's condition resulting from medication therapies. Referring now to FIG. 10, an optional practice guideline 149 supplements the structure of the point of care system of FIG. 4. The practice guideline 149 provides references for practitioners to consult regarding courses of action to obtain a diagnosis and alternative treatments for various conditions. The practice guideline 149 communicates with the patient data capture 140, the clinical data capture 142 and the encounter data capture 146 to assist the practitioner in selecting the appropriate course of action. The practice guideline 149 likewise communicates with the progress notes 144 to provide a healthcare provider with a historical context of the patient's condition and alternative treatments already attempted.

Figure 11:
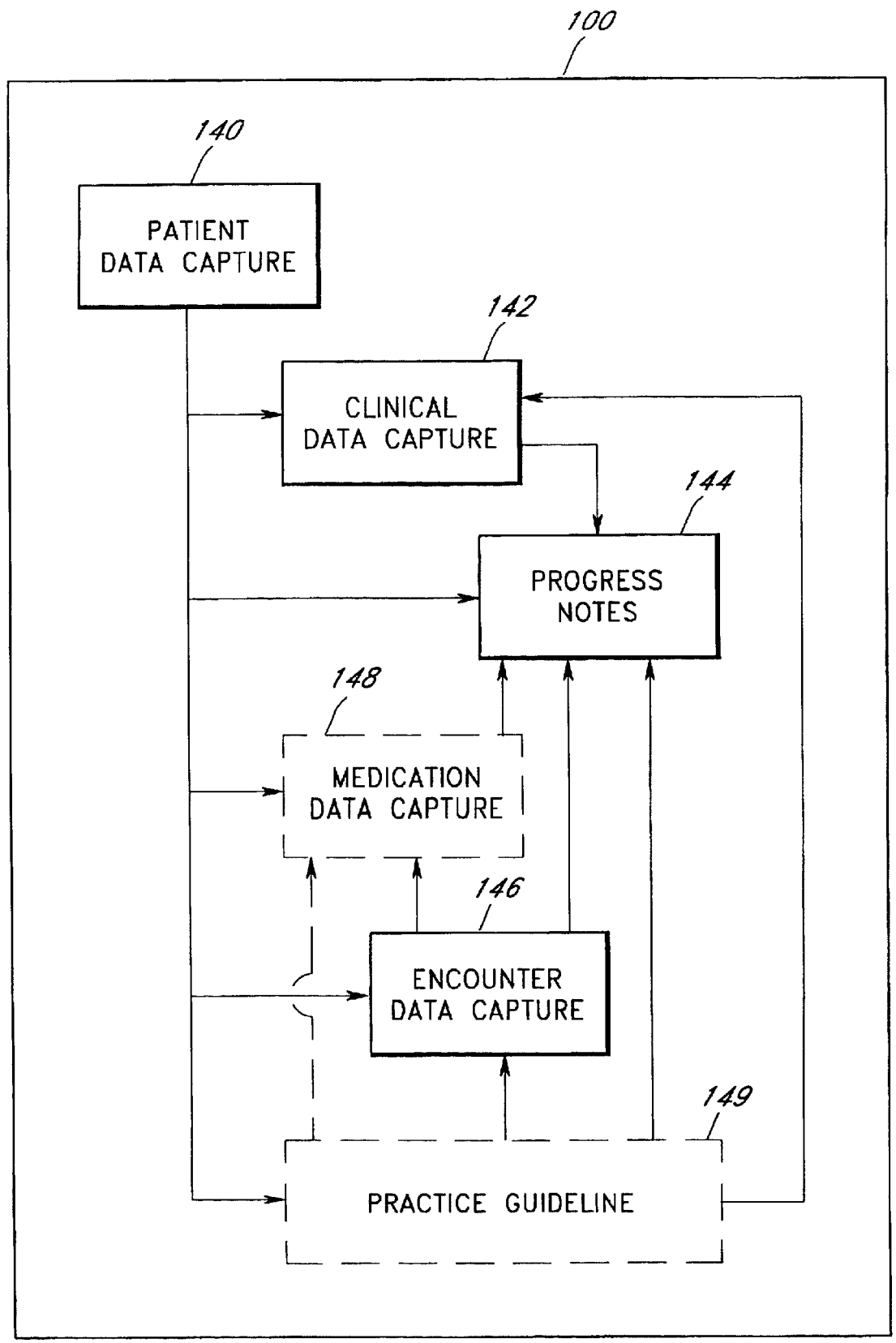
FIG. 11 is a block diagram illustrating the structure of the medication data capture and the practice guideline in the point of care system of FIG. 4.

FIG. 11 shows a point of care system 100 having a medication data capture 148 and a practice guideline 149. As before, the medication data capture 148 communicates with the patient data capture 140 and with the progress note 144. Similarly, the practice guideline 149 communicates with patient data capture 140, the clinical data capture 142, the encounter data capture 146 and the progress note 144. However, the practice guideline 149 may now communicate with the medication data capture 148 to address situations where accepted practice guidelines require a healthcare provider to prescribe and administer medications. In a preferred embodiment, the point of care system 100 includes the graphical user interface illustrated in FIG. 5. Referring back to FIG. 5, the patient chart window 150 includes tabs for medication data 191 and practice guidelines 193 that activate the medication data capture 148 and the practice guideline 149, respectively. Similarly, pressing the medication manager button 192 activates the medication data capture 148 and the practice guideline 149. A healthcare provider can enter, review and annotate patient medication data and practice guideline data as described previously.

Figure 12:
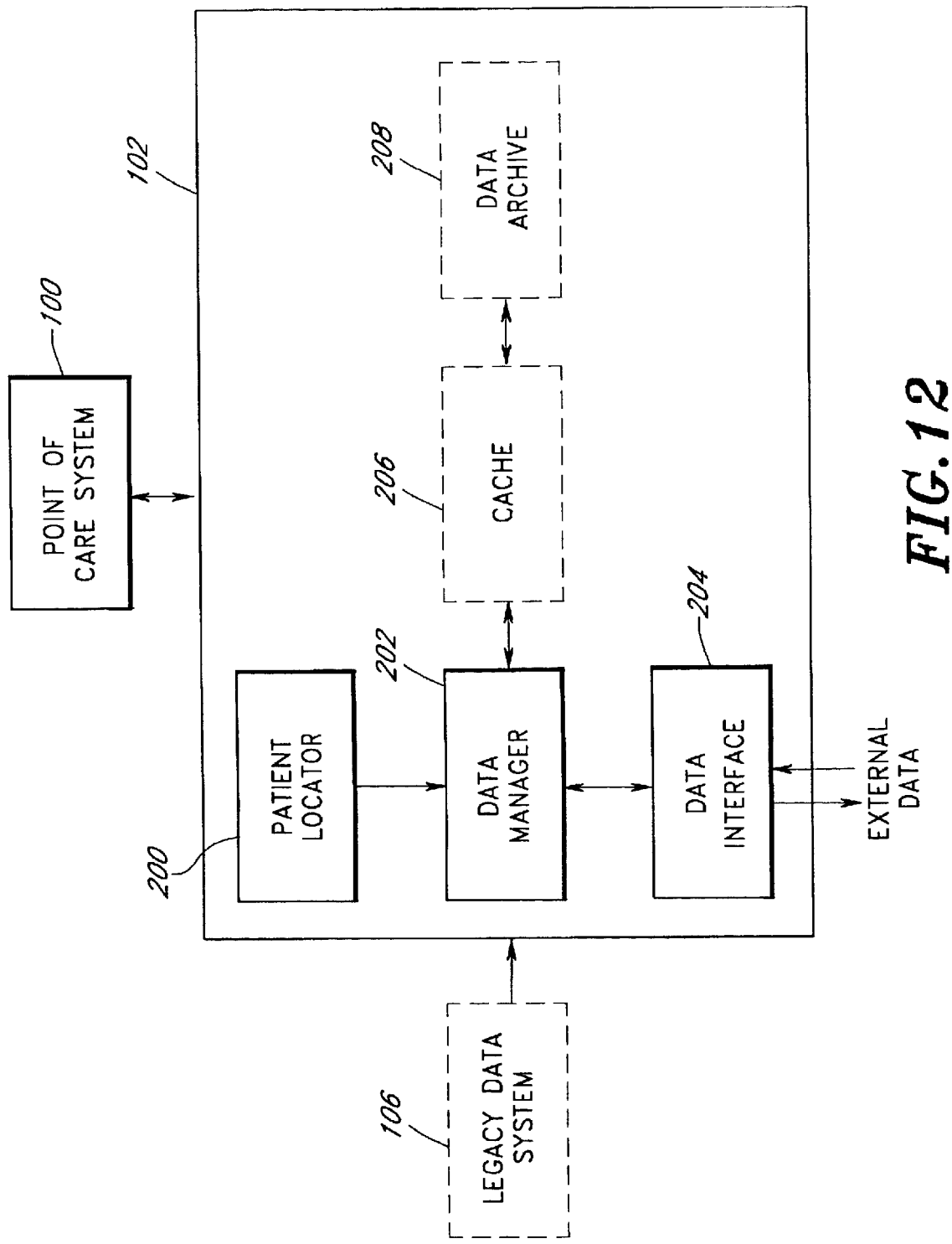
FIG. 12 is a block diagram illustrating the structure of the patient data repository of FIG. 1.

Referring now to FIG. 12, a block diagram illustrates the structure of the patient data repository 102. The patient data repository 102 includes a patient locator 200, a data manager 202 and a data interface 204. The patient locator 200 generates a unique patient identifier (PID) 221 (FIG. 14) for each patient and creates and maintains a table having PIDs for all patients who have data in the patient data repository 102. All data records related to a patient 211, 212, 213, 214, 215, 216, 219 include and reference the patient's unique PID as shown in FIG. 13.

Figure 13:
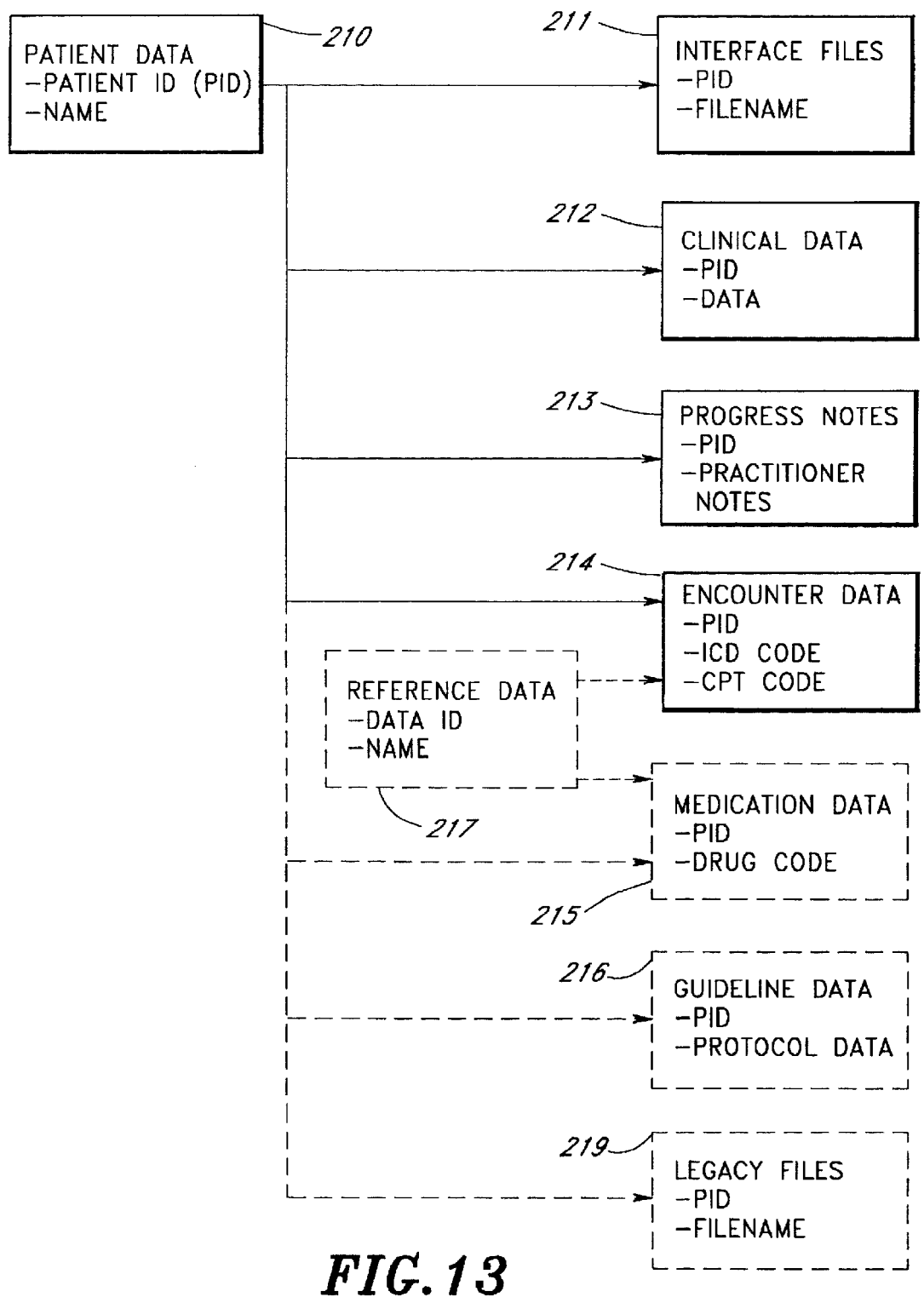
FIG. 13 is a block diagram illustrating the structure of a patient record within the patient data repository of FIG. 12.

With reference to FIG. 13, upon creation of a patient record, the patient locator 200 creates a patient data structure 210 having the PID and the patient's name. In a preferred embodiment, the patient data structure 210 includes pointers to data structures having data within a patient record captured by the point of care system 100 and incorporated from external sources (e.g., a digital x-ray image file stored in a raster pixel format). Thus, the patient data structure 210 maintains a pointer to an interface files structure 211 having patient data transmitted from external sources. The patient data structure 210 likewise maintains pointers to a clinical data structure 212, a progress note structure 213 and an encounter data structure 214. These data structures include patient data captured by the clinical data capture 142, progress notes 144 and encounter data capture 146, respectively (FIG. 4). In another preferred embodiment, the patient data structure 210 may include pointers to data structures having data generated by the reference database 104 and transferred by the legacy data system 106. Thus, the patient data structure 210 may maintain pointers to a medication data structure 215 and a guideline data structure 216. As described above, the medication 215 and guideline 216 data structures include patient data captured by the medication data capture 148 and the practice guideline 149, respectively. In this embodiment, a reference data structure 217 may maintain pointers to the encounter data structure 214 and to the medication data structure 215 for access to reference information contained in a reference database 104. Lastly, the patient data structure 210 may maintain a pointer to a legacy files structure 219 having patient data transmitted from the legacy data system 106, such as an image of a patient chart.

Figure 14:
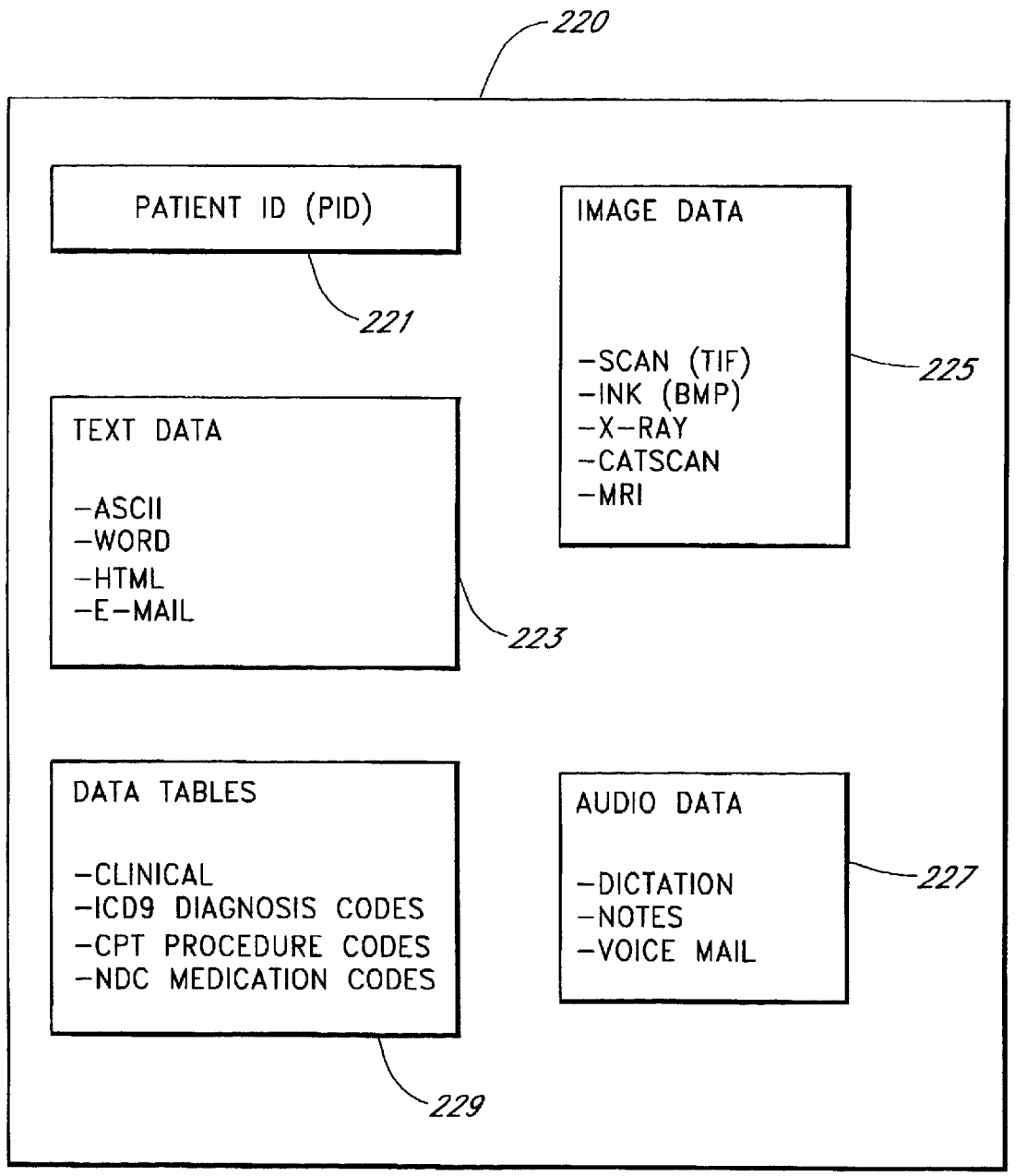
FIG. 14 is an example of the patient record of FIG. 13.

FIG. 14 shows a logical view of a patient record 220 corresponding to the structure illustrated in FIG. 13. The patient record 220 includes the PID generated by the patient locator 200 (FIG. 12) in the patient data repository 102 (FIG. 1). In addition, the patient record 220 includes patient data in a variety of data types generated by healthcare providers. Thus, the patient record includes text data 223, such as electronic mail and word processing documents from other healthcare providers, image data 225, such as scanned physical documents, x-rays and CATSCANs, and audio data 227, such as a physician's dictation and voice mail. Lastly, the patient record 220 has data tables 229, such as a physician's ICD9 diagnosis codes and CPT procedure codes. In view of the structure of a patient record 220, referring back to FIG. 12, the data manager 202 uses the PID to store and retrieve patient records. Moreover, the data interface 204 permits communication with external sources to obtain patient data, such as demographic data, laboratory test results and x-ray images, and to transfer patient information, such as prescriptions for medication, from the patient data repository 102 to external healthcare providers.

With reference to FIG. 12, the patient data repository 102 may optionally include a cache 206 for temporary storage of patient data and a data archive 208 for long term storage of patient data. In this embodiment, the data manager 202 coordinates the transfer of patient data to and from a data archive 208 into a cache 206. For example, the data manager 202 may identify patient records that a healthcare provider needs for appointments scheduled at a future time and then transfer these patient records from the data archive 208 into the cache 206 for quick access prior to the scheduled appointment. Similarly, the data manager 202 may purge from the cache 206 records of patients who have not had recent appointments and whose records are already archived. The data manager 202 likewise tracks the location and description of patient data within the data archive 208 by associating the file name of the patient data within a patient record 220 with the patient identifier 221. When possible, the data manager 202 will group data associated with a patient within the data archive 208 for rapid retrieval in a manner similar to files within a directory in an operating system. Thus, the data manager 202 assigns a directory to each patient identifier and then stores patient data within this directory.

Figure 15A:
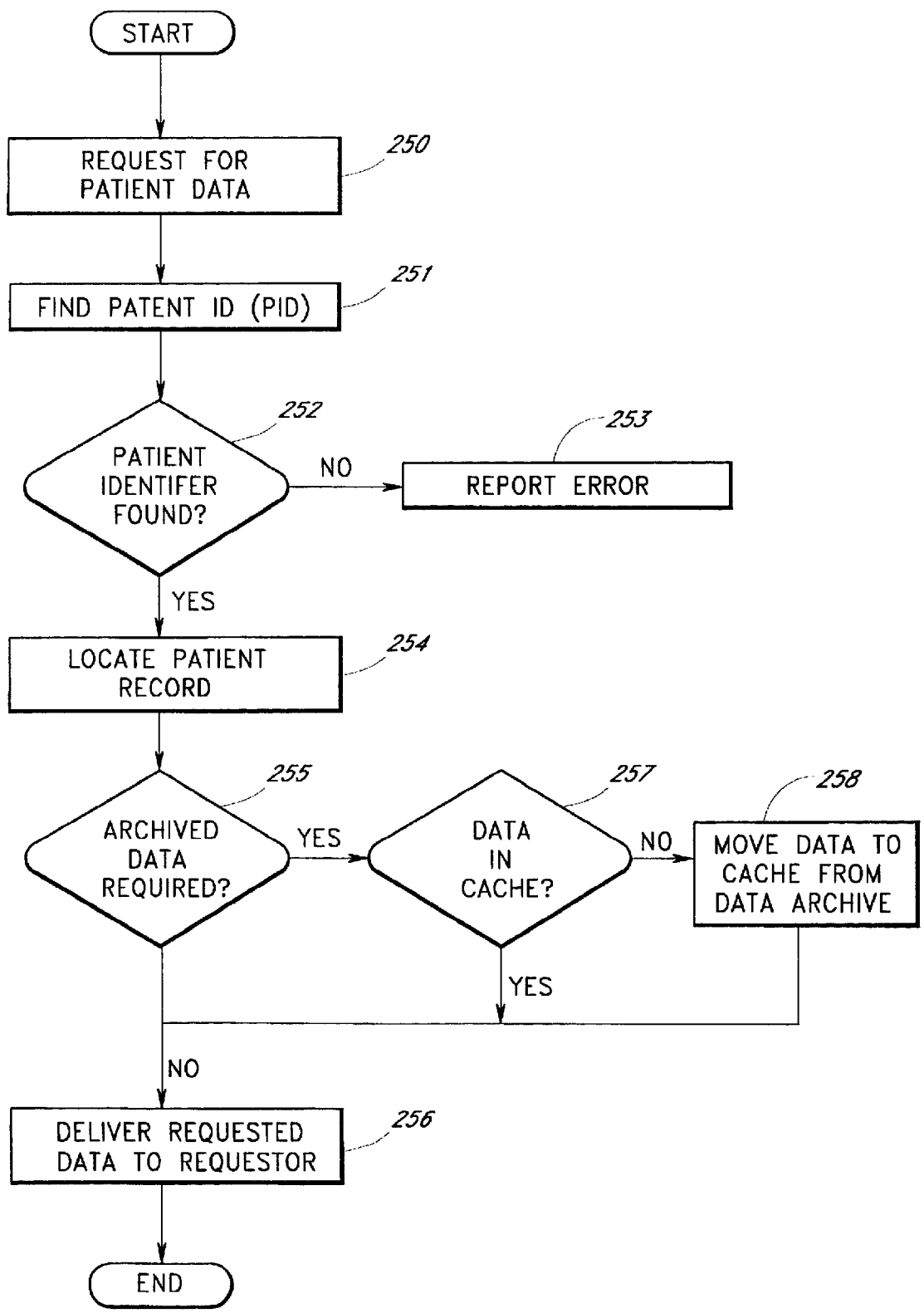
FIG. 15*a* is a flowchart illustrating the process flow of the patient data repository of FIG. 12.

FIG. 15a illustrates the process flow for the patient data repository 102 (FIG. 1). For example, the point of care system 100 (FIG. 1) issues a request for patient data 250. With reference to FIGS. 15a and 12, the patient locator 200 receives the request from the point of care system 100 and, at 251 attempts to find the PID for the record having the requested patient data. As determined at 252, if no PID is found, the patient locator 200 reports an error 253. At this point, the patient data repository 102 (FIG. 1) may recover from the error 253 by either restarting the process or by ending the process. Otherwise, the patient locator 200 communicates the PID to the data manager 202. The data manager 202 locates the patient record using the PID at 254. As determined at 255, in a system without cache 206 and without a data archive 208, the data manager 202 delivers the requested data 256 to the point of care system 100. In a system having a cache 206 and a data archive 208, the data manager 202 determines at 257 if the requested data exists in the cache 206. If so, the data manager 202 delivers the requested data 256 to the requester from the cache 206. Otherwise, the data manager 202 first moves the data 258 from the data archive 208 to the cache 206 and then delivers the requested data 254 to the requester from the cache 206.

Figure 15B:
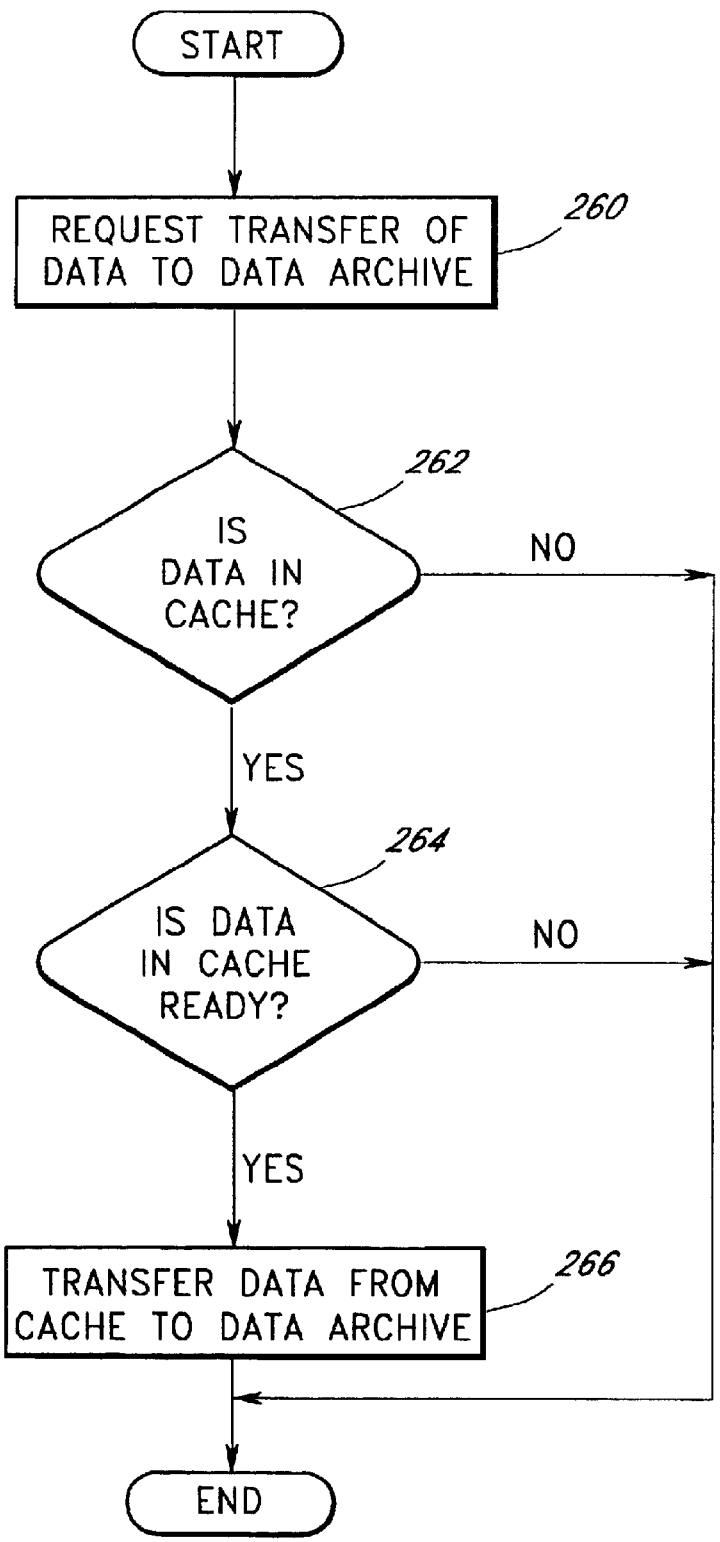
FIG. 15*b* is a flowchart illustrating the process for a transfer of data from a cache to a data archive in the patient data repository of FIG. 12.

In addition, FIG. 15b, in conjunction with FIG. 12, illustrates the process for transferring data from a cache 206 to a data archive 208. The data manager 202 monitors the contents of the cache 206. To improve the performance of the cache 206, the data manager 202 requests transfer 260 of data to the data archive 208 under certain conditions. For example, the data manager 202 may purge the cache 206 when data requested for storage in the cache would exceed its memory capacity. In this circumstance, the data manager 202 first transfers to the data archive 208 signed files and then data files in chronological order, i.e., oldest files first. Similarly, a healthcare provider can specify a predetermined time, such as 3 calendar days, or other selected conditions for transfer to the data archive 208. As determined at 262, if the cache 206 does not have the data to transfer, the process ends as the data manager 202 ignores the request. As determined at 264, if the data in the cache 206 is not ready for transfer, the process ends and the data manager 202 queues the request for the next transfer of data to the data archive 208. Data in the cache 206 is ready for transfer when a physician has reviewed and accepted it and when it has not been previously committed to the data archive 208. Otherwise, the data manager 202 transfers data from the cache 206 to the data archive 208 at 266.

Figure 16:
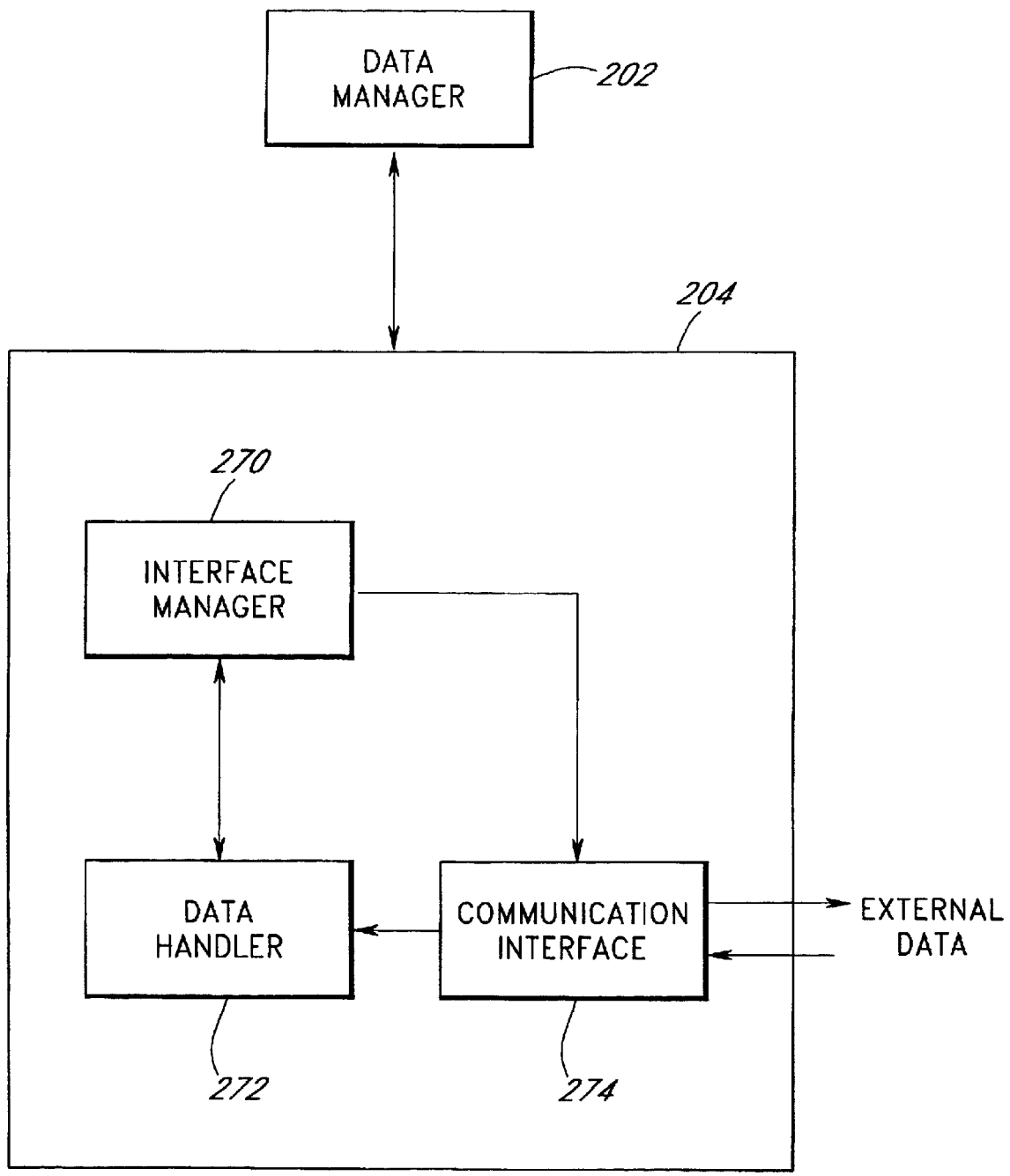
FIG. 16 is a block diagram illustrating the structure of the data interface of FIG. 12.

Referring now to FIG. 16, the data interface 204 of the patient data repository 102 includes an interface manager 270, a data handler 272 and a communication interface 274. To transfer and receive patient data from external sources (not shown), the interface manager 270 communicates with a data handler 272 and a communication interface 274. In addition, the communication interface 274 communicates with the data handler 272 for conversion of received external patient data into formats recognized by the EMR system. The interface manager 270 creates and maintains an interface registry of data formats for external sources. Prior to data transfer or receipt by the EMR system, the interface manager 270 registers an interface for an external source. Upon registration of an interface, the interface manager 270 can provide the appropriate conversion routines for the data handler 272 to use for transfer of data to and receipt of data from an external source. These conversions are well understood by the relevant technologist.

Figure 17A:
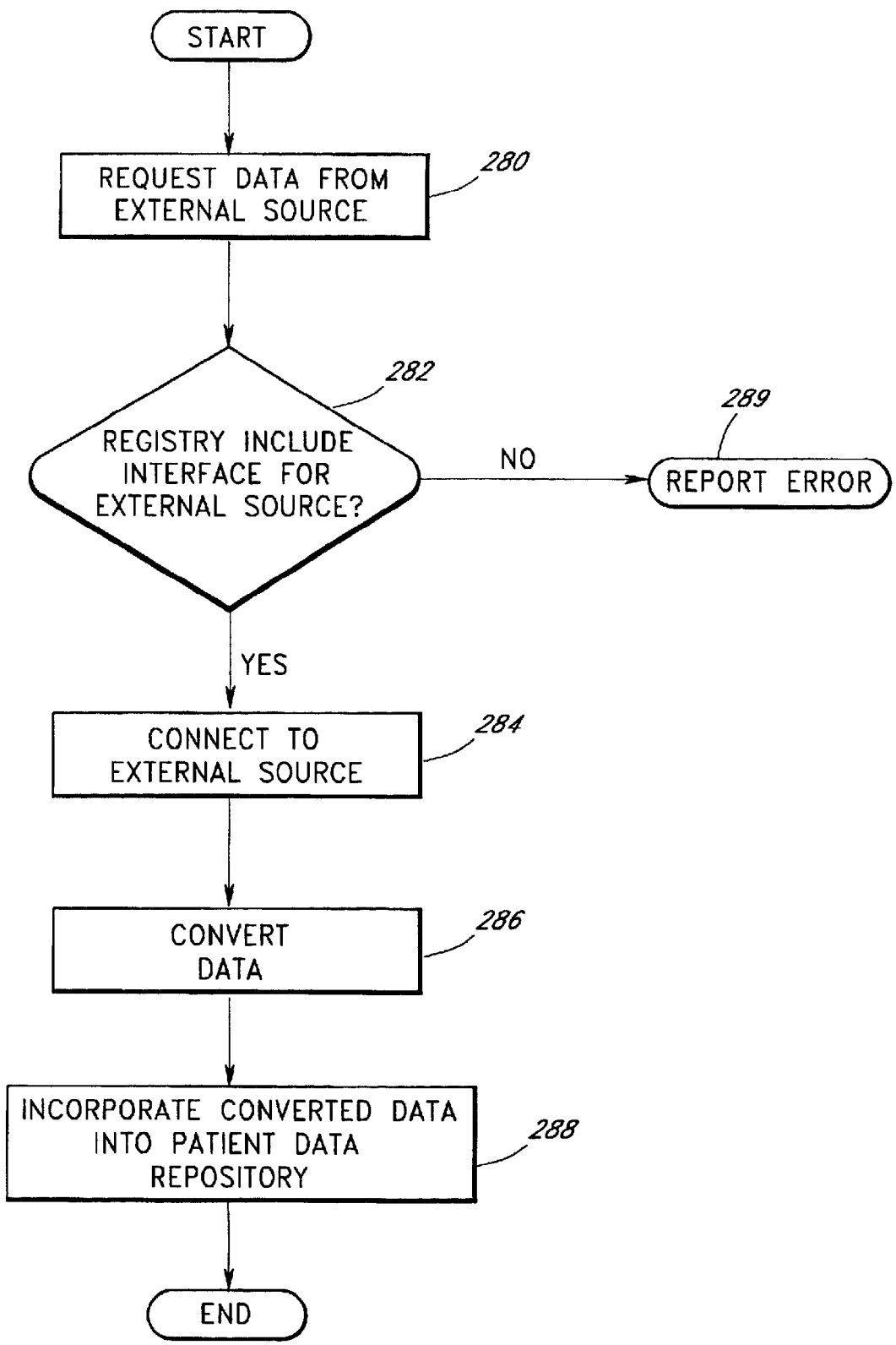
FIG. 17*a* is a flowchart illustrating the process flow of the data interface of FIG. 16 when receiving patient data from an external source.
Figure 17B:
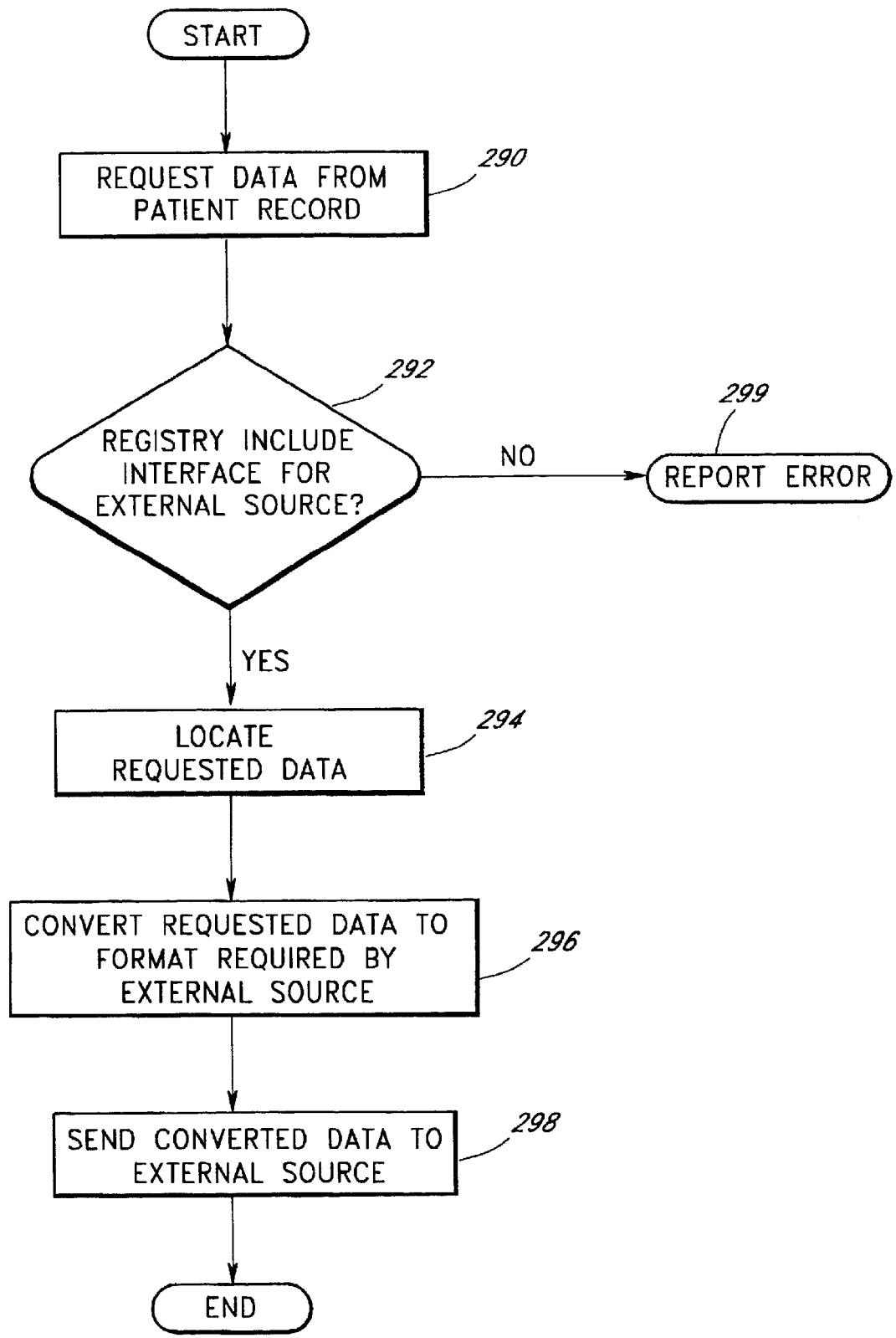
FIG. 17*b* is a flowchart illustrating the process flow of the data interface of FIG. 16 when transmitting patient data to an external source.

FIGS. 17a and 17b illustrate the operation of the data interface 204 of the patient data repository 102 (FIG. 12). Referring now to FIG. 17a, the data manager 202 issues a request 280 for patient data from an external source. At 282, the interface manager 270 determines if the registry includes an interface for the external source, such as a laboratory or pharmacy. As determined at 282, if the registry includes an interface for the external source, the communication interface 274 connects to the external source 284 to receive patient data. The data handler 272 retrieves the appropriate conversion routine for the external source to convert data 286. In a preferred embodiment, the data handler 272 converts data from an external source into a database table for the appropriate PID. Lastly, the data manager 202 incorporates converted data 288 into the patient record. Otherwise, the interface manager 270 reports an error 289. The data manager 202 may recover from the error 289 in several ways. First, the data manager 202 may invoke a module to register an interface for the external source so as to allow the process to continue. Second, the data manager 202 may end the process at this point. Lastly, the data manager 202 may restart the process in the event the external source was specified incorrectly.

Referring now to FIG. 17b, an external source requests data 290 from a patient record. As described above, the interface manager 270 determines at 292 if the registry includes an interface for the external source. As determined at 292, if the registry includes an interface for the external source, the data manager 202 locates the requested data at 294 and the data handler 272 converts requested data at 296 to the format required by the external source. The communication interface 274 then sends the converted data to the external source at 298. For example, the patient data repository 102 may transmit a physician's prescription for medication to a hospital or pharmacy. If the registry includes no interface for the external source, the interface manager 270 reports an error 299. Similarly, as discussed above for the process flow of FIG. 17a, the interface manager 270 may recover from the error 299 by restarting the process, ending the process or invoking a module to register the external source to allow the process to continue.

Figure 18:
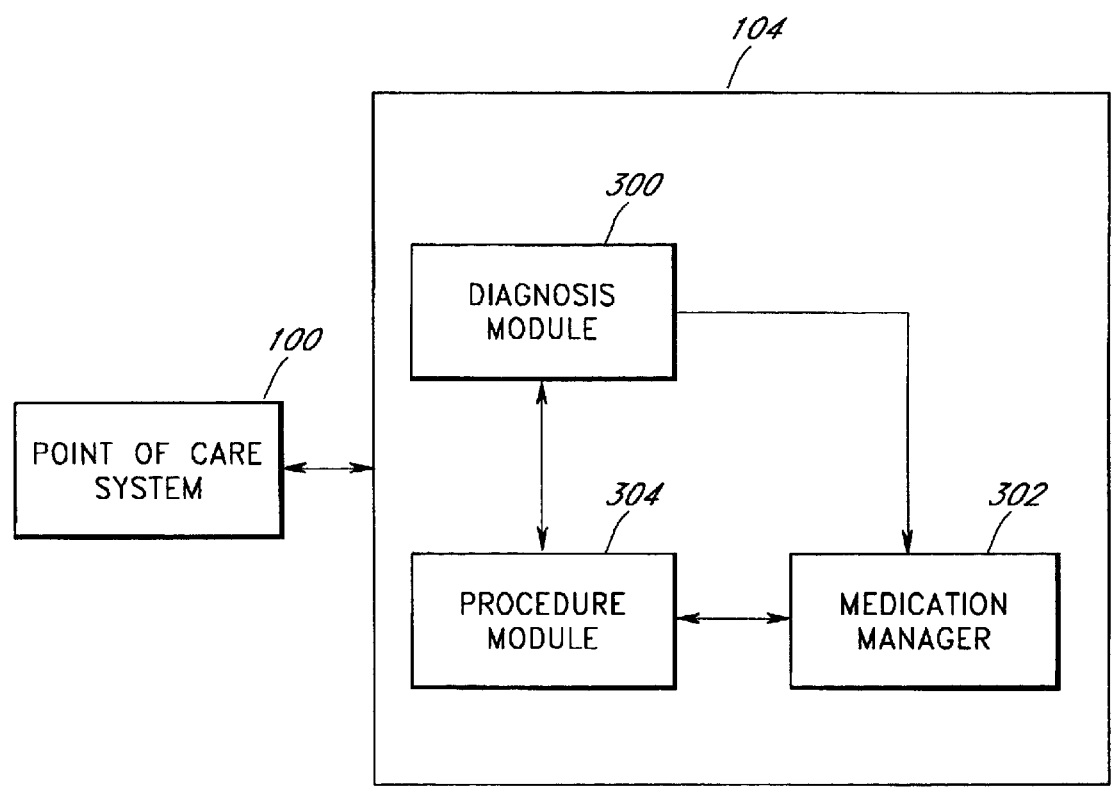
FIG. 18 is a block diagram illustrating the structure of the reference database of FIG. 1.

Referring now to FIG. 18, a block diagram illustrates the structure of the optional reference database 104 (FIG. 1). The reference database 104 includes a diagnosis module 300, a medication manager 302 and a procedure module 304. A healthcare provider can use the reference database 104 for assistance in diagnosing a patient's disease, prescribing medications and ordering supplemental procedures to treat the disease. The diagnosis module 300 communicates with a medication manager 302 to obtain information on medications indicated by a diagnosis. The medication manager 302 provides information on medications, such as proper dosages, allergies, contraindications, adverse interactions with other medications, and side effects. The diagnosis module 300 likewise communicates with a procedure module 304 to obtain information on the proper administration of procedures indicated by a diagnosis. The procedure module 304 provides information on procedures for treatment as indicated by the diagnosis. In many instances, the medication manager 302 communicates with the procedure module 304 regarding the administration of various medications.

In a preferred embodiment, the point of care system 100 provides access to the reference database 104 through a graphical user interface having a patient chart window 310 shown in FIG. 19. A healthcare provider accesses the diagnosis module 300 and the procedure module 304 by pointing and clicking on a reference access button 312.

As shown in FIG. 20, the reference access button 312 produces a reference window 330 including the graphical interfaces for the diagnosis module 300 and the procedure module 304. For example, to enter a diagnosis, a physician clicks on the scroll down button 331 adjacent to the system box 332 to produce a list of body systems. The physician selects the appropriate system and the diagnosis module 300 enters the selected system in the system box 332 and provides a list having specific diagnosis codes for the selected body system in the diagnosis box 334. The physician then selects the appropriate diagnosis code and clicks on the add button 336 adjacent to the diagnosis selection box 337. The diagnosis module 300 enters the selected diagnosis code to the diagnosis selection box 337. The physician may repeat the above steps to add multiple diagnosis codes to the diagnosis selection box 337. In a similar manner, a physician uses the scroll down button 331 adjacent to the topic box 333 to select the appropriate procedure topic. The procedure module 304 enters the selected procedure topic in the topic box 333 and provides a list of procedure codes in the procedure box 335. The physician now selects the appropriate procedure code and adds it to the procedure selection box 338 by clicking on the add button 336 adjacent to the procedure selection box 338. The physician may likewise repeat the above steps to add multiple procedure codes to the procedure selection box 338. The physician completes entry of diagnoses and procedures by clicking on the done button 339 to return to the patient chart window 310 of FIG. 19.

Figure 21:
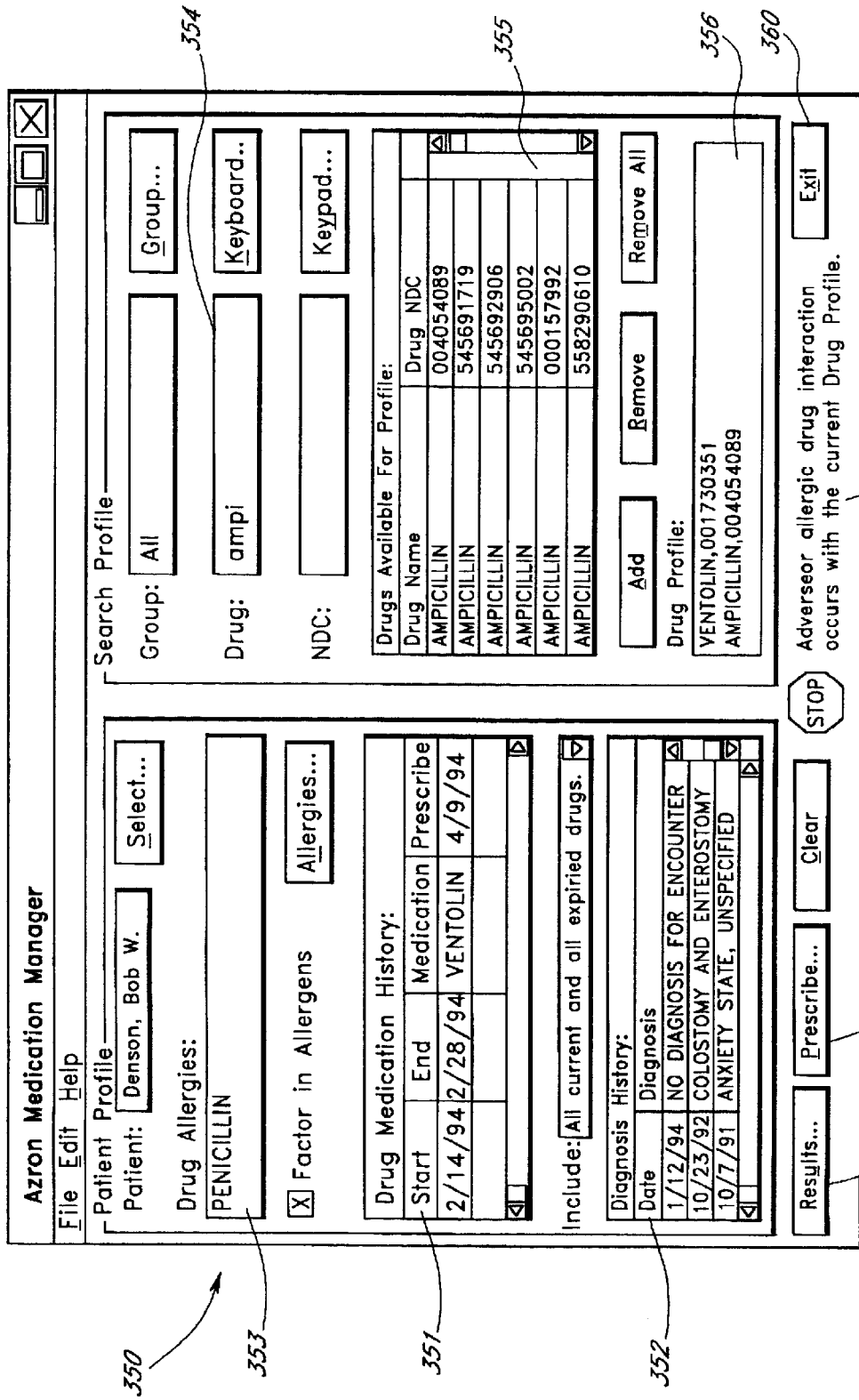
FIG. 21 shows an example of a graphical user interface for the medication manager of the reference database of FIG. 18.

The healthcare provider similarly accesses the medication manager 302 (FIG. 18) by clicking on a medication button 192 (FIG. 19). Referring now to FIG. 21, the medication button 314 activates a medication manager window 350. The physician can review the patient's history by viewing the medication history box 351 and the diagnosis history box 352 before prescribing any new medications. The physician can also review any patient allergies in the allergy box 353. The physician can select a medication by entering the name of the medication in the name box 354. Note that as the physician enters the root letters of a medication name, a list of medications with the root letters appears in the medication list box 355. As before, the physician selects a medication from the list by clicking on it and the medication manager 302 places the selected medication in a selection box 356. If there are no contraindications or allergies for the patient, the physician prescribes the medications listed in the selection box 356 by clicking on the prescribe button 357.

Figure 22:
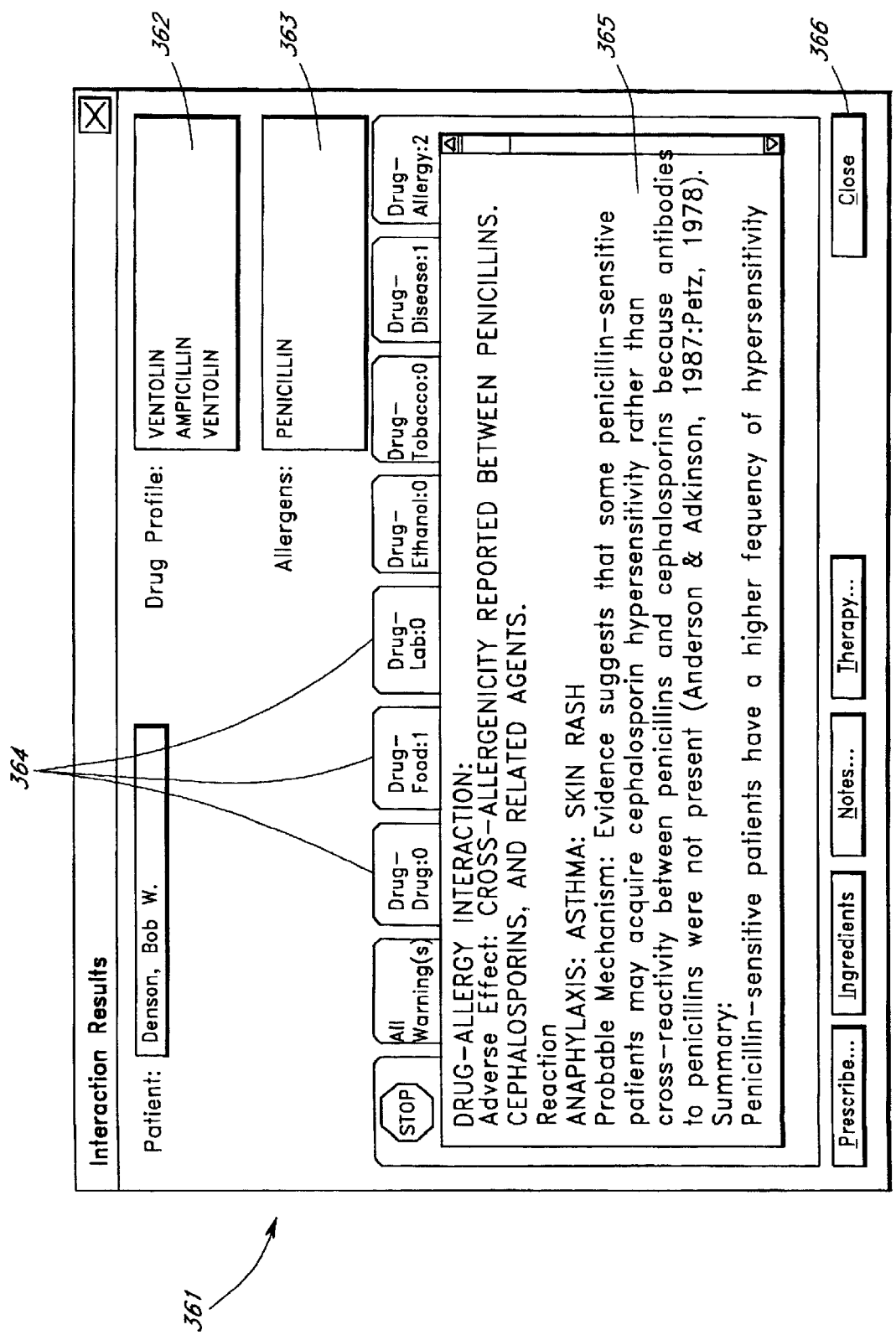
FIG. 22 shows an example of a medication interaction window of the medication manager of FIG. 21.

Otherwise, if a contraindication exists, a warning appears in a warning bar 358 to alert the physician. In view of the warning, the physician can investigate the effects of the medication by clicking on the results button 359. Referring now to FIG. 22, the results button produces a medication interaction window 361. A medication selection box 362 displays the medications selected and under consideration by the physician. An allergy list box 363 displays the patient's allergens. Folder tabs 364 include labels describing the medication combinations and interactions. The physician clicks on one of these folder tabs 364 to display the contents of the folder in the viewing box 365. The physician can then evaluate the information on the interaction including potential adverse patient reactions. The physician clicks on the done button 366 to return to the medication manager window 350 of FIG. 21. The physician can make any needed revisions to the medications selected in the manner described above. Afterwards, the physician exits the medication manager 302 by clicking on the exit button 360.

Figure 23:
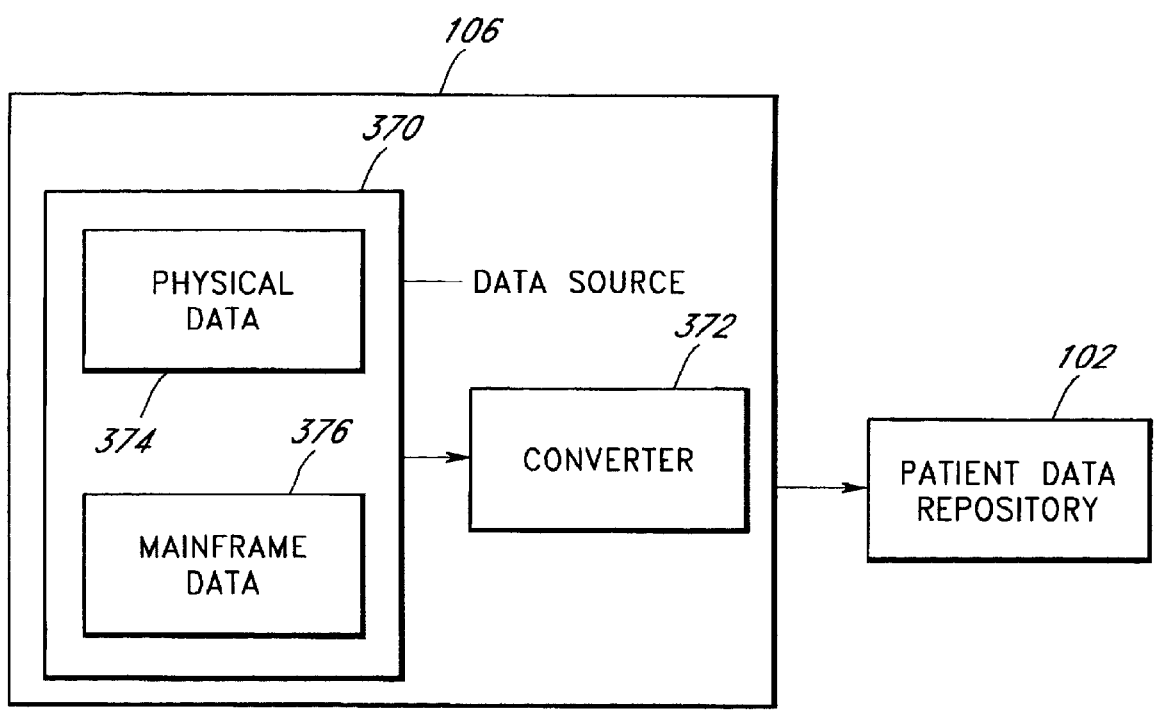
FIG. 23 is a block diagram illustrating the structure of the legacy data system of FIG. 1.

Referring now to FIG. 23, a block diagram illustrates the structure of the optional legacy data system 106 as shown in FIG. 1. The legacy data system 106 includes a data source 370 and a converter 372. The data source 370 comprises physical data 374, such as paper based records and photographs, and electronic mainframe data 376. The converter 372 receives information from the data source 370 and transforms the information into an electronic format compatible with the EMR system. For example, to input physical data 374, such as paper or image based data, into a patient record, the converter 372 comprises a scanner to digitize the physical data into a binary file format for incorporation into the patient's record. To input electronic mainframe data 376, the converter 372 employs the same mechanism used for transfer or receipt of patient data from external sources. As described before, the converter 372 determines if an interface exists for the mainframe data, selects the appropriate data handler and converts the data into the proper format for incorporation into a patient record.

II. EMR System Configurations

Figure 24:
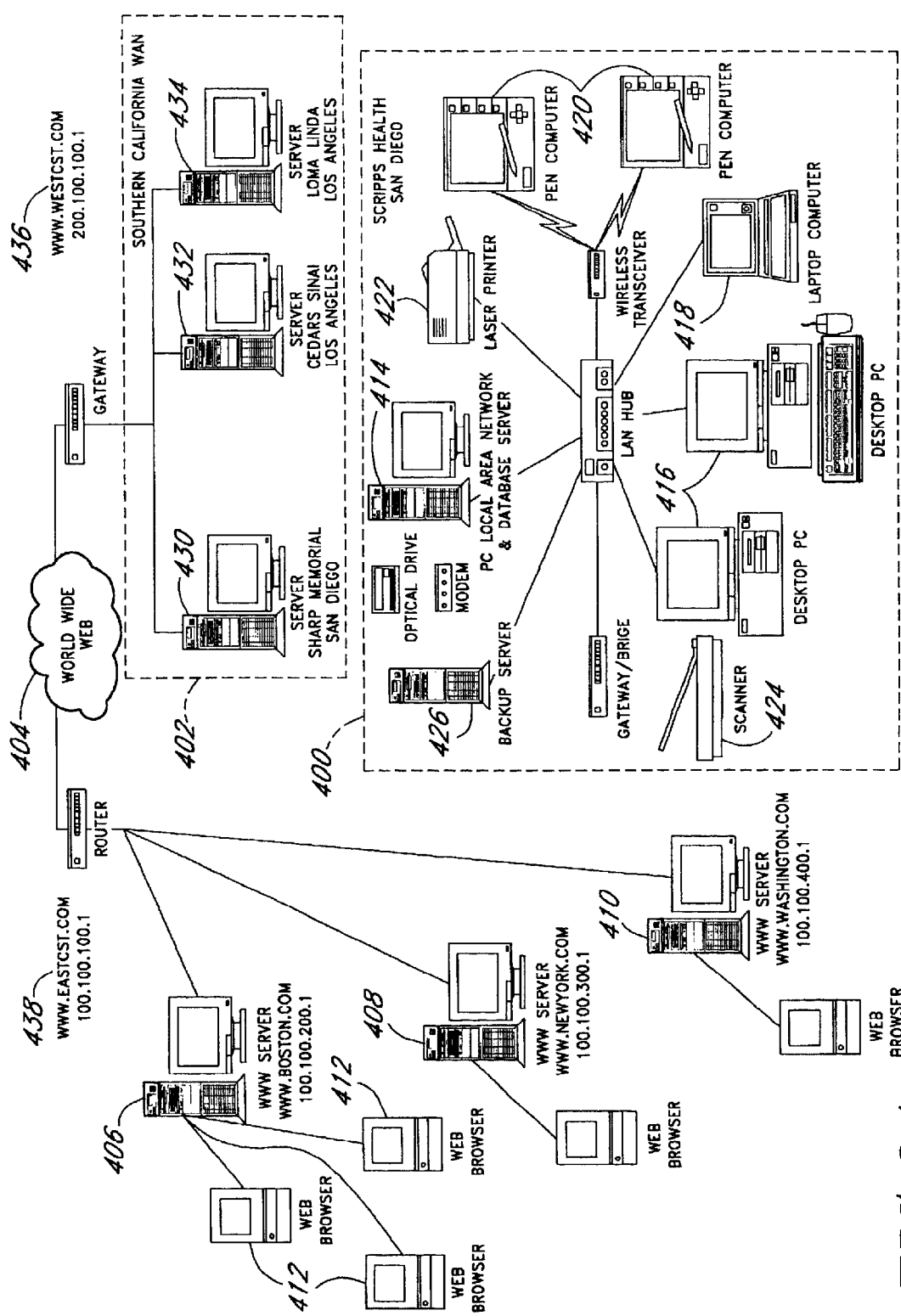
FIG. 24 is an example of a typical configuration for the electronic medical records system of the present invention.

FIG. 24 illustrates one possible configuration for the EMR system of the present invention. The system comprises a wide area network (WAN) 402, the World Wide Web (Web) 404 portion of the Internet, and remote web servers 406, 408, 410 communicating with web browsers 412. The WAN 402 comprises a plurality of local area network (LAN) servers supporting local and remotely located healthcare providers. For example, the WAN 402 includes LANs supporting Scripps Health 414 and Sharp Memorial 430 in San Diego and Cedars Sinai 432 and Loma Linda 434 in Los Angeles, Calif. In one presently preferred embodiment, the server comprises a multi-processor personal computer having Intel Pentium processors, such as a Compaq Proliant 4500R 5/100 Model 2, communicating with a fault tolerant, error correcting storage device, such as a Hewlett Packard 20XT Optical Jukebox having 20 gigabytes of storage capacity. The LAN 400 includes a backup server 426 and several peripherals, such as a scanner 424 to input documents and a laser printer 422 to print out documents. In a preferred embodiment, the LAN backbone comprises an Ethernet twisted pair cable configured in a general star topology. Similarly, the scanner 424 comprises a Fujitsu M3093EX scanner using Kofax KIPP ImageControls software and the laser printer 422 comprises a Hewlett Packard LaserJet 4Plus. Healthcare providers may access the LAN 400 using a desktop computer 416, a laptop computer 418 or wireless pen computer 420. In a preferred embodiment, the desktop computer 416 comprises a Compaq Deskpro 5/75 Model 630, the laptop computer 418 comprises a IBM ThinkPad 760CD and the pen computer 420 comprises a Fujitsu Stylist 1000 configured with a Solectek AirLAN PCMCIA network adapter for wireless LAN access. The EMR system also provides for communication through the World Wide Web. For example, remote healthcare providers may access the WAN 402 on the Web using the domain name "www.westcst.com" 436. Thus, a healthcare provider located in Boston, Mass. may access a patient record resident on the Scripps Health server 414, located in San Diego, Calif., using a web browser 412, such as Microsoft Explorer or Netscape Navigator, communicating with a Web server in Boston, Mass. having the domain name "www.boston.com" 406.

In a preferred embodiment, servers 414, 426, desktop 416, or laptop 418 computers and peripherals, such as printers 422 or scanners 424, communicate with each other and with the Web using a network operating system, such as Microsoft Windows NT, Windows 95 or Windows for Workgroups. Similarly, pen computers 420 use the Microsoft Windows for Pen Computing operating system. In another preferred embodiment, the servers, computers and peripherals communicate using an operating system supporting Web browsers on computer networks, such as Unix, Novell Netware or Apple System 7.0. In yet another preferred embodiment, the EMR system includes servers, computers and peripherals networked using mixed network operating systems, such as Unix, Netware and Windows. For example, the LAN 400 may operate on a Windows NT network operating system, whereas the LAN 430 may operate on an Apple System 7.0 network, and the Web server "www.boston.com" 406 may operate on a Unix operating system. Thus, the EMR system supports communication among a variety of hardware components, such as printers 422, scanners 424 and pen computers 420, using a variety of network operating systems, such as Windows, Netware or Unix. In a preferred embodiment, healthcare providers, such as clinics and laboratories, may also communicate with the EMR system using modem links and standard v0.34 modem devices, such as a US Robotics Sportster 28,800 modem.

The EMR system includes several databases of electronic information, such as the medication manager 302 and the data manager 202. In a preferred embodiment, the EMR system implements a relational database language that conforms to American National Standards Institute (ANSI) standard SQL-92, a 580 page specification for the SQL relational database language. A database language standard specifies the semantics of various components of database management systems (DBMS). In particular, it defines the structures and operations of a data model implemented by the DBMS, as well as other components that support data definition, data access, security, programming language interface and data administration. The SQL-92 standard specifies data definition, data manipulation, and other associated facilities of a DBMS that supports the relational data model. SQL is old in the art and additional information on SQL-92 is available in ANSI specification X3.135-1992, hereby incorporated by reference.

Similarly, in another preferred embodiment, relational databases in the EMR system support the Open Database Connectivity (ODBC) model. ODBC is an application program interface (API) that allows client applications running under Microsoft Windows to access data from a variety of data sources, including relational and non-relational DBMS. These data sources may reside on a client machine or they may be located on a remote server communicating through a network common to the client machine. Under ODBC, data sources may vary in complexity from shrink-wrap databases, such as Microsoft Access, running under Windows on a client machine to more sophisticated, proprietary relational DBMS running on a Unix server or mainframe computer. For a client application to access data from a data source, a dynamic link library (DLL) driver must exist for each data source to be accessed. For additional information on ODBC is available from Inside ODBC, by Karl Geiger, hereby incorporated by reference.

II. Summary

The electronic medical record system of the present invention advantageously overcomes several limitations of existing technologies and alternatives. Because it is more efficient and cost effective to move data, instead of physical records and healthcare providers, the present invention eliminates the need to create and maintain any physical data records. In contrast to other systems, the present invention creates and maintains all patient data electronically. Thus, there is no need to find, pull, move, update, file and replace physical charts. As a result, healthcare providers no longer require substantial shelving and storage space for physical files. The present invention likewise eliminates the mishandling, loss and destruction of patient data typically associated with maintenance of physical data records.

Using the present invention, healthcare providers enter patient data immediately at the point of care. Thus, the EMR system captures each piece of data at its source at the time of entry, including time and healthcare provider identification. The EMR system thus provides a complete audit trail for all patient data. The audit trail, in turn, permits inexpensive analysis of outcomes, utilization and compliance. For example, outcomes typically refer to the effectiveness of a treatment plan. Thus, the EMR system enables a healthcare provider to analyze patient recovery times and incurred costs to measure the efficacy of the treatment plan. Similarly, utilization typically refers to how well available resources are utilizing time. Thus, the EMR system provides the capability to analyze utilization of physicians, nurses, staff and equipment as well as time utilization for patients, such as wait times for referrals, lab results and physician examinations. Lastly, compliance typically refers to conformance with government and accreditation standards and regulations. The EMR system provides tools to enable healthcare providers to measure conformance to standards and regulations. To facilitate entry of patient data at the point of care, the invention provides touch screens for entry of lab orders, medications, diagnoses and procedures. The invention likewise provides instant access to a patient's electronic medical record by authorized healthcare providers from any geographical location. Thus, the EMR system enables authorized healthcare providers to access and update patient files using wireless pen-based personal computers. In addition, authorized healthcare providers can access a record while other healthcare providers use the same record. By providing simultaneous access to patient data, the present invention enables real-time collaboration among multiple healthcare providers.

The availability of electronic data permits instant, sophisticated analysis of a patient's clinical data. Thus, the EMR system can create graphs of a patient's vital signs and lab results or the system can provide an analyze patient information to identify medication interactions and allergies. Using the present invention, a healthcare provider can likewise select, sort, and analyze patient data to identify relationships among the data considered. In addition, the EMR system provides flexibility in the creation and maintenance of patient data repositories. Thus, the present invention can support a large healthcare enterprise distributed across a large geography as well as a single physician office. Moreover, the present invention ensures patient confidentiality through the use of a tiered password system. The EMR system provides several levels of security for access to patient data. For example, a system administrator may have global password access to any patient data for system maintenance and debug purposes, whereas physicians may have access only to patient records within their specialty and nurses and staff may have access to only those patient records within their immediate care. In addition, a patient may request restricted access to their data by only certain personnel. Thus, in contrast to physical records, the EMR system provides superior protection of patient data.

In addition, the present invention is useful in legal, manufacturing and general administration environments. For example, the present invention is capable of organizing, maintaining and protecting legal files in an attorney's office. Thus, the EMR system can store and retrieve scanned images of paper documents, such as deeds and assignments, as well as other native file formats, such as word processing files. The EMR system organizes and retrieves this data in a manner akin to that of a patient's medical record. Upon entry of a client data into the EMR system, attorneys can annotate documents, transfer information to and from other systems, or create new data for automatic filing in the client or case file. Similarly, the EMR system is useful for management of procurement or regulatory data in a manufacturing context. Thus, the EMR system can organize and maintain material safety data sheets (MSDS) as well as other data pertinent to materials procurement, such as conformance to specification measurements and inspection data for received lots, in a manufacturing environment. Lastly, the EMR system is useful for general administrative files in any organization. For example, the present invention is applicable to employee files in human resources, customer files in sales and approved suppliers in procurement. The EMR system can organize and retrieve data within these files in the manner as patient data in a patient data record. As discussed above, upon entry of a data into the EMR system, users can annotate documents, transfer information to and from other systems, or create new data for automatic filing in the respective file.

Those skilled in the art may practice the principles of the present invention in other specific forms without departing from its spirit or essential characteristics. Accordingly, the disclosed embodiments of the invention are merely illustrative and do not serve to limit the scope of the invention set forth in the following claims.

What is claimed is:

1. A medical records system, comprising:
    a point of care system to capture patient data at a point of care; and
    a patient data repository, in communication with the point of care system and with external systems, to store and organize the patient data for access by the point of care system.

* * * * *